US009545515B2

(12) United States Patent
Wolpaw et al.

(10) Patent No.: US 9,545,515 B2
(45) Date of Patent: Jan. 17, 2017

(54) SYSTEM AND RELATED METHOD TO RESTORE AND/OR IMPROVE NERVOUS SYSTEM FUNCTIONS BY MODIFYING SPECIFIC NERVOUS SYSTEM PATHWAYS

(71) Applicant: Health Research, Inc., Menands, NY (US)

(72) Inventors: Jonathan R. Wolpaw, Delmar, NY (US); Gerwin Schalk, Glenmont, NY (US); Aiko K. Thompson, Garnerville, NY (US); Peter Brunner, Albany, NY (US); Xiang Yang Chen, Albany, NY (US); Dennis J. McFarland, Albany, NY (US)

(73) Assignee: Health Research, Inc., Menands, NY (US)

( * ) Notice: Subject to any disclaimer, the term of this patent is extended or adjusted under 35 U.S.C. 154(b) by 0 days.

(21) Appl. No.: 14/855,879

(22) Filed: Sep. 16, 2015

(65) Prior Publication Data

US 2016/0067492 A1    Mar. 10, 2016

Related U.S. Application Data

(63) Continuation of application No. 14/502,295, filed on Sep. 30, 2014, now Pat. No. 9,138,579, which is a (Continued)

(51) Int. Cl.
*A61N 1/00* (2006.01)
*A61N 1/36* (2006.01)
(Continued)

(52) U.S. Cl.
CPC ......... *A61N 1/36014* (2013.01); *A61B 5/0488* (2013.01); *A61B 5/0492* (2013.01);
(Continued)

(58) Field of Classification Search
CPC ............ A61B 2562/046; A61B 5/0488; A61B 5/0492; A61B 5/4848; A61B 5/6828; A61B 5/742; A61N 1/0456; A61N 1/0476; A61N 1/36003; A61N 1/36014; A61N 1/36082; A61N 1/36103; A61N 2001/36039
See application file for complete search history.

(56) References Cited

U.S. PATENT DOCUMENTS 5,643,332 A    7/1997  Stein
5,814,093 A    9/1998  Stein
(Continued)

OTHER PUBLICATIONS

Thompson et al., "Acquisition of a Simple Motor Skill: Task-Dependent Adaptation Plus Long-Term Change in the Human Soleus H-Reflex," *The Journal of Neuroscience*, 29(18):5784-5792 (2009).

(Continued)

*Primary Examiner* — George Manuel
(74) *Attorney, Agent, or Firm* — Heslin Rothenberg Farley & Mesiti P.C

(57) ABSTRACT

The present invention provides methods, devices, and systems for restoring or improving nervous system function of a subject. Provided is a method involving: (i) providing an operant conditioning protocol effective to produce targeted neural plasticity (TNP) in a primary targeted central nervous system (CNS) pathway of a subject; and (ii) administering the operant conditioning protocol to the subject to elicit TNP in the primary targeted CNS pathway and to elicit generalized neural plasticity (GNP) in one or more other CNS pathway. The elicitation of the GNP in the one or more other CNS pathway serves to restore or improve a nervous system function of the subject. Provided is a device comprising a nerve stimulation-electromyographic recording component and a controller for operating the nerve stimulation-electro- (Continued)

myographic recording component in accordance with an operant conditioning protocol.

31 Claims, 17 Drawing Sheets

Related U.S. Application Data continuation of application No. 13/958,181, filed on Aug. 2, 2013, now Pat. No. 8,862,236.

(60) Provisional application No. 61/678,671, filed on Aug. 2, 2012.

(51) Int. Cl.
*A61B 5/0488* (2006.01)
*A61N 1/04* (2006.01)
*A61B 5/0492* (2006.01)
*A61B 5/00* (2006.01)

(52) U.S. Cl.
CPC ............ *A61B 5/4848* (2013.01); *A61B 5/742* (2013.01); *A61N 1/0456* (2013.01); *A61N 1/0476* (2013.01); *A61N 1/36003* (2013.01); *A61N 1/36082* (2013.01); *A61N 1/36103* (2013.01); *A61B 5/6828* (2013.01); *A61B 2562/046* (2013.01); *A61N 2001/36039* (2013.01)

(56) References Cited

U.S. PATENT DOCUMENTS

| | | |
|---|---|---|
| 7,269,456 B2 | 9/2007 | Collura |
| 7,899,556 B2 | 3/2011 | Nathan et al. |
| 8,000,794 B2 * | 8/2011 | Lozano ............ A61N 1/36014 607/45 |
| 2005/0084880 A1 | 4/2005 | Duman et al. |
| 2009/0105786 A1 | 4/2009 | Fetz et al. |
| 2012/0229270 A1 | 9/2012 | Morley et al. |
| 2012/0330395 A1 | 12/2012 | Dar et al. |

OTHER PUBLICATIONS

Knash et al., "Electrical stimulation of the human common peroneal nerve elicits lasting facilitation of cortical motor-evoked potentials," *Experimental Brain Research*, 153(3):366-377 (2003).

Makihara et al., "H-Reflex Modulation in the Human Medial and Lateral Gastrocnemii During Standing and Walking," *Muscle & Nerve*, 45:116-125 (2012).

Chen et al., "Operant Conditioning of H-Reflex Can Correct a Locomotor Abnormality after Spinal Cord Injury in Rats," *The Journal of Neuroscience*, 26(48):12537-12543 (2006).

Chen et al., "Operant Conditioning of Rat Soleus H-Reflex Oppositely Affects Another H-Reflex and Changes Locomotor Kinematics," *The Journal of Neuroscience*, 31(31):11370-11375 (2011).

Chen et al., "Reflex conditioning: A new strategy for improving motor function after spinal cord injury," *Annals of New York Academy of Science*, 1198(Suppl 1):E12-E21 (2010).

Thompson et al., "Short-term effects of functional electrical stimulation on motor-evoked potentials in ankle flexor and extensor muscles," *Experimental Brain Research*, 159(4):491-500 (2004).

Thompson et al., "Short-term effects of functional electrical stimulation on spinal excitatory and inhibitory reflexes in ankle extensor and flexor muscles," *Experimental Brain Research*, 170(2):216-226 (2006).

Ferris et al., "Soleus H-reflex gain in humans walking and running under simulated reduced gravity," *Journal of Physiology*, 530(1):167-180 (2001).

Thompson et al., "Operant Conditioning of a Spinal Reflex Can Improve Locomotion after Spinal Cord Injury in Humans," *The Journal of Neuroscience*, 33(6):2365-2375 (2013).

\* cited by examiner

A. Session schedule

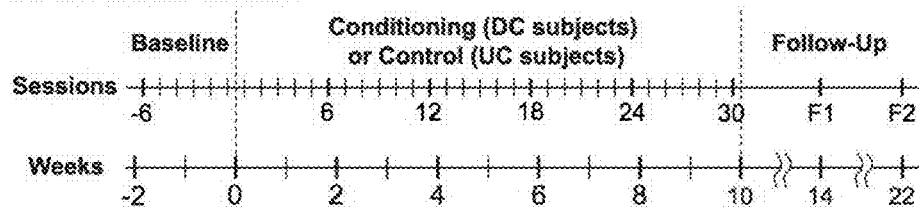

B. Session composition

|  | Unconditioned (UC) Subjects | Down-Conditioning (DC) Subjects |
|---|---|---|
| Baseline Sessions | H-M recruitment curve 225 Control Trials (three 75-trial blocks) | |
| Control / Conditioning Sessions & Follow-Up Sessions | H-M recruitment curve 225 Control Trials (in three 75-trial blocks) | H-M recruitment curve 20 Control Trials 225 Conditioning Trials (in three 75-trial blocks) |

C. Visual feedback screens

Control trials

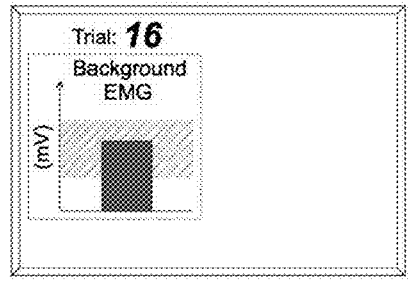

Conditioning trials

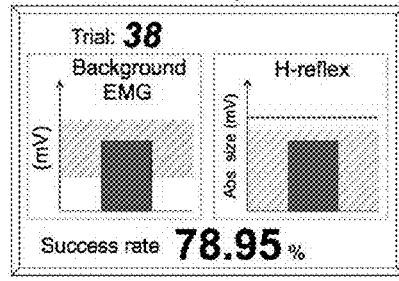

FIGS. 11A-11C

SYSTEM AND RELATED METHOD TO RESTORE AND/OR IMPROVE NERVOUS SYSTEM FUNCTIONS BY MODIFYING SPECIFIC NERVOUS SYSTEM PATHWAYS

CROSS-REFERENCE TO RELATED APPLICATIONS

This application is a continuation of U.S. patent application Ser. No. 14/502,295, filed Sept. 30, 2014, which is a continuation of U.S. patent application Ser. No. 13/958,181, filed Aug. 2, 2013, now U.S. Pat. No. 8,862,236, issued Oct. 14, 2014, which claims priority benefit of U.S. Provisional Patent Application Ser. No. 61/678,671, filed Aug. 2, 2012, the disclosures of which are hereby incorporated by reference herein in their entirety.

GOVERNMENT RIGHTS STATEMENT

This invention was made with Government support under grant numbers NS069551, NS022189, NS061823, and HD036020 awarded by the National Institutes of Health. The United States Government has certain rights in the invention.

FIELD OF THE INVENTION

The present invention generally relates to the field of neurological rehabilitation. In certain embodiments, the present invention relates to methods, devices, and systems for restoring and/or improving nervous system function of a subject.

BACKGROUND OF THE INVENTION

The primary goal of neurological rehabilitation is to restore important motor and cognitive skills that have been impaired by injury or disease. Current therapeutic methods consist primarily of the repeated practice of these skills (e.g., treadmill locomotion, reach and grasp actions) (Wernig and Muller, 1992; Edgerton et al., 1997; Harkema et al., 1997; Taub et al., 1999; Wernig et al., 2000; Edgerton et al., 2001; Maegele et al., 2002; Taub and Uswatte, 2003; Wolf et al., 2006; Edgerton et al., 2008), with the expectation that this practice will lead to plasticity that improves function (Koski et al., 2004; Thickbroom et al., 2004; Thomas and Gorassini, 2005; Yen et al., 2008). Although this strategy is logical and often beneficial, it is seldom completely successful.

The skills that rehabilitation attempts to restore normally depend on plasticity throughout the central nervous system (CNS), from the cerebral cortex to the spinal cord (Drew et al., 2002; Nielsen, 2002; Hultborn and Nielsen, 2007; Wolpaw, 2010; Rossignol and Frigon, 2011). Moreover, the location and nature of the damage that impairs performance differ widely from individual to individual, as well as from disorder to disorder. As a result, the plastic changes (i.e., persistent changes) needed to restore a particular skill (e.g., locomotion) are also likely to differ widely across individuals. Thus, new therapeutic methods that can induce plasticity in particular CNS pathways, and can thereby target each individual's particular deficits, might significantly increase the effectiveness of rehabilitation.

In both animals and humans, operant conditioning protocols can modify specific spinal reflex pathways (Wolpaw and O'Keefe, 1984; Wolpaw, 1987; Chen and Wolpaw, 1995; Wolf and Segal, 1996; Carp et al., 2006a; Chen et al., 2006a; Thompson et al., 2009). Because these spinal pathways participate in important skills such as locomotion, conditioning protocols might be used to reduce the functional deficits produced by spinal cord injuries, strokes, and other disorders. An initial animal study supports this hypothesis. In rats in which a lateralized spinal cord injury (SCI) had produced a gait asymmetry, appropriate conditioning of the soleus H-reflex on the injured side eliminated the asymmetry and restored more normal locomotion (Chen et al., 2006b).

The spinal stretch reflex (SSR) (i.e., the tendon jerk) and its electrical analog, the H-reflex are the simplest motor behaviors. They are produced primarily by a two-neuron, monosynaptic pathway comprised of the primary afferent fiber, its synapse on the motoneuron, and the motoneuron itself (Wolpaw et al., 1983, Wolpaw, 1987). Because it is affected by descending activity from the brain, this pathway can be operantly conditioned. In response to a conditioning protocol, monkeys, humans, rats, and mice can gradually increase (i.e., up-conditioning) or decrease (i.e., down-conditioning) the SSR or the H-reflex (Wolpaw 2010 for review). The larger or smaller reflex that results is a simple motor skill (i.e., "an adaptive behavior acquired through practice" (Chen et al. 2005)). H-reflex conditioning is accompanied by neuronal and synaptic plasticity at multiple sites in the spinal cord and brain (Wolpaw and Chen 2009 for review).

H-reflex conditioning is a powerful model for exploring the mechanisms and principles of skill acquisition and maintenance (Wolpaw 2010). The spinal cord is the final common pathway for all motor behavior, and spinal cord plasticity has a part in the acquisition and maintenance of many motor skills. Furthermore, by virtue of their simplicity, accessibility, separation from the brain, and closeness to behavior, the spinal cord in general and the H-reflex in particular are uniquely suited for studying how activity-dependent plasticity (particularly gradual plasticity) explains behavior, and for formulating concepts and identifying principles that may apply to learning throughout the CNS.

Because the spinal cord is the final common pathway for motor output, the spinal cord plasticity associated with H-reflex conditioning affects other behaviors. For example, in normal rats, right soleus muscle H-reflex up- and down-conditioning produce corresponding changes in the right soleus burst during locomotion (Chen et al. 2005). Nevertheless, despite this change, the right/left symmetry of the step cycle is preserved. This suggests that changes in other reflex pathways compensate for the locomotor effects of the change in the soleus H-reflex pathway. This hypothesis is supported by other evidence that the functional effects of H-reflex conditioning extend beyond the conditioned reflex, and even to the contralateral side of the spinal cord (Wolpaw and Lee 1989).

To date, there is generally a lack of methods, devices, and systems that can be used by subjects and patients to restore and/or improve nervous system functions, particularly in a self-administered or outpatient manner. Therefore, novel strategies that can complement current methods and thereby enhance and/or restore important motor and cognitive skills that have been impaired by injury or disease are needed.

The present invention is directed to overcoming the current deficiencies in the art of neurological rehabilitation.

SUMMARY OF THE INVENTION

The present invention relates to methods, devices, and systems for restoring and/or improving nervous system function of a subject. In a general sense, the present invention provides new and useful methods, devices, and systems for use in the field of neurological rehabilitation. In addition, the present invention provides new and useful methods, devices, and systems for use by those who wish to improve and/or reach their optimal performance potential with respect to their central nervous system (CNS) sensorimotor and/or cognitive functions (e.g., athletic performance, memory skills, etc.).

In one aspect, the present invention provides a method for restoring or improving nervous system function of a subject. This method involves the steps of (i) providing an operant conditioning protocol effective to produce targeted neural plasticity (TNP) in a primary targeted central nervous system pathway of a subject; and (ii) administering the operant conditioning protocol to the subject under conditions effective to elicit TNP in the primary targeted CNS pathway and to elicit generalized neural plasticity (GNP) in one or more other CNS pathway. The elicitation of the GNP in the one or more other CNS pathway serves to restore or improve a nervous system function of the subject.

In another aspect, the present invention provides a device for restoring or improving nervous system function of a subject. The device comprises a nerve stimulation-electromyographic recording component and a controller for operating the nerve stimulation-electromyographic recording component in accordance with an operant conditioning protocol. The a nerve stimulation-electromyographic recording component comprises a nerve stimulator for stimulating a primary targeted central nervous system pathway in a subject, at least one stimulating electrode array in functional communication with the nerve stimulator and adapted for topical contact with the subject, and at least one electromyographic (EMG) recording electrode array for recording EMG data of the subject produced in response to the stimulation of the primary targeted CNS pathway. As mentioned, the device also comprises a controller for operating the nerve stimulation-electromyographic recording component in accordance with an operant conditioning protocol. The operant conditioning protocol is effective to produce targeted neural plasticity (TNP) in the primary targeted CNS pathway of the subject.

In certain embodiments, the device of the present invention further comprises a wearable placement component for positioning the at least one stimulating electrode array at a stimulation target area of the subject and/or for positioning the at least one EMG recording electrode array at an EMG recording target area of the subject.

In certain other embodiments, the device of the present invention further comprises a wireless communication device for receiving, displaying, storing, and/or analyzing data generated by the controller.

In one aspect, the present invention relates to a novel method for restoring and/or improving central nervous system sensorimotor and/or cognitive functions.

The discovery of the method for improving important CNS functions by using operant conditioning protocols to produce targeted neural plasticity (TNP) in specific central nervous system (CNS) pathways was first reported in by the present inventors in Thompson et al., 2013. In a first embodiment, the method of the present invention used it to improve walking in people in whom a chronic incomplete spinal cord injury (SCI) had produced a spastic gait disorder characterized by hyperactive reflexes, abnormal reflex modulation in ankle extensor muscles, and/or weak ankle dorsiflexion leading to foot drop (Dietz and Sinkjaer, 2007, Nielsen et al., 2007, Barthelemy et al., 2010). Because of these abnormalities, the subjects walked very slowly and with great difficulty, and usually needed an assistive device such as crutches or a walker. By down-conditioning the soleus H-reflex in the most impaired leg, the present invention greatly reduced these abnormalities and markedly improved the entire behavior of walking; muscles in both legs behaved more normally and contributed more effectively to walking. The subjects walked faster and more symmetrically (i.e., they limped less), and the modulation of muscle activity across the step cycle increased in both legs. Furthermore, they commented spontaneously that they were walking faster and farther in their daily lives, and a number noted less abnormal reflex activity, easier stepping, less dependence on an assistive device, and/or other improvements. These first results showed that the methods provides a valuable new approach to restoring useful function after spinal cord injuries and probably in other neuromuscular disorders as well. Example 2 provides a full description of one embodiment of the first demonstration of the method.

This discovery that the method had extremely broad beneficial impact on an important motor skill (i.e., walking) was wholly unexpected and not predictable from previously available knowledge. The discovery indicates that this novel method provides an entirely new approach to improving standard neuromuscular skills, such as walking, or special skills, such as athletics, that are normally improved through repeated practice of the skills and/or parts of them. As noted herein, this new method modifies specific nervous system pathways through an operant conditioning protocol. These pathway-specific changes (i.e., targeted neural plasticity (TNP)) have widespread effects on the complex nervous system networks that produce neuromuscular skills, and they can thereby improve these skills beyond the levels possible with conventional practice. The method can improve neurorehabilitation in people with disabilities due to spinal cord injury, stroke, cerebral palsy, brain injury, or other disorders. It may also enable people without disabilities to reach levels of skill performance beyond those possible through conventional practice (e.g., athletes, dancers, etc.). In sum, the present invention can, inter alia, improve neuromuscular skills, and potentially cognitive skills as well, to levels beyond those reachable through conventional practice. Further, to implement the method in a portable and/or subject-administered manner, provided herein are devices and systems that are used to perform the method of the present invention.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 9A: Average final locomotor H-reflexes (in % of their initial values) of $SOL_R$ and $QD_R$ muscles for successful HRup (left) and HRdown (right) rats. P values for difference from initial value by paired t-test are shown. *: P<0.05; **: P<0.01. FIG. 9B: Effects of $SOL_R$ HRup and HRdown conditioning on the locomotor H-reflexes in representative rats. Average post-stimulus $SOL_R$ and $QD_R$ EMG in the stance phase of locomotion during the control-mode (solid) and near the end of conditioning (dashed) for an HRup rat and an HRdown rat. After HRup conditioning, the $SOL_R$ H-reflex is larger and the $QD_R$ H-reflex is smaller, while after HRdown conditioning the $SOL_R$ H-reflex is smaller and the $QD_R$ H-reflex is larger. Pre-stimulus EMG (EMG at time zero) and M-responses are stable. Peaks in the first 1-2 ms after stimulation are stimulus artifacts.

FIGS. 11A-11C are illustrations of various aspects of one embodiment of the present invention. FIG. 11A is a session schedule. Six Baseline sessions were followed by 30 Conditioning (DC subjects) or Control (UC subjects) sessions, and then by two Follow-up sessions. FIG. 11B is a Composition of Baseline, Control, Conditioning, and Follow-up sessions. FIG. 11C shows visual feedback screens for Control and Conditioning trials.

FIG. 12A: Final Conditioned H-reflex sizes (i.e., average for the last 3 Conditioning sessions) for individual Conditioning (DC) and Unconditioned (UC) subjects. The data for normal DC subjects are from Thompson et al. (2009). The filled triangles represent the DC subjects whose Conditioned H-reflexes for the last 6 Conditioning sessions were significantly less than their H-reflexes for the 6 Baseline sessions. The open triangles represent the DC subjects in whom the H-reflex did not decrease significantly. (The lowest open triangle failed to reach statistical significance due to high inter-session variability.) FIGS. 12B and 12C: Average Conditioned (FIG. 12B) and Control (FIG. 12C) H-reflexes for a Baseline session (solid) and the last Conditioning session (dashed) from a DC subject with SCI in whom the H-reflex decreased significantly. Both Conditioned and Control H-reflexes are smaller after 30 Conditioning sessions. As summarized in FIGS. 13A and 13B, the decrease in the Control H-reflex is nearly as great as that in the Conditioned H-reflex. Background EMG and M-wave do not change. A small stimulus artifact is present.

FIGS. 13A and 13D: Average Conditioned H-reflex size. FIGS. 13B and 13E: Average Control H-reflex size. FIGS. 13C and 13F: Average of Conditioned H-reflex size minus Control H-reflex size (i.e., task-dependent adaptation (see Results)). (see Thompson et al. (2009) for details). In the subjects with SCI, the Conditioned H-reflex decreases to 69% of the baseline value over 30 Conditioning sessions (FIG. 13A). This decrease consists of a relatively small task-dependent adaptation (−7%, FIG. 13C) and a relatively large across-session Control reflex decrease (−24%, FIG. 13B). In the subjects without disability (Thompson et al., 2009), the Conditioned H-reflex also decreases to 69% of the baseline value over 24 Conditioning sessions (FIG. 13D). This decrease consists of a relatively large task-dependent adaptation (−15%, FIG. 13F) and a relatively small across-session Control reflex decrease (−16%, FIG. 13E). The asterisks between FIGS. 13B and 13E and between FIGS. 13C and 13F indicate significant differences (p<0.01) between subjects with SCI and normal subjects in final Control H-reflex value and in task-dependent adaptation, respectively. Task-dependent adaptation is greater in the normal subjects, while change in the Control H-reflex is greater in the subjects with SCI.

FIG. 14A: Average (±SE) 10-m walking speeds after 30 Conditioning or Control sessions (in % of Baseline speed) for subjects in whom the H-reflex did or did not decrease significantly. FIG. 14B: Step-cycle symmetry before (open bars) and after (shaded bars) 30 Conditioning or Control sessions for subjects in whom the H-reflex did or did not decrease significantly. Symmetry is measured as the ratio of the time between the nonconditioned leg's foot contact (nFC) and the conditioned (or simply stimulated, in the case of UC subjects) leg's foot contact (cFC) to the time between cFC and nFC. A ratio of 1 indicates a symmetrical gait. Initially, the ratio is >1. After the 30 Conditioning or Control sessions, the ratio has decreased toward 1 in the subjects in whom the H-reflex decreased while it has increased in the subjects in whom the H-reflex did not decrease. FIG. 14C: Successive step cycles before and after conditioning from a subject in whom the H-reflex decreased. Each nFC (●) and cFC (○) is shown. The short vertical dashed lines mark the midpoints between nFCs (i.e., the midpoints of the step-cycle), which is when cFC should occur. Before H-reflex down-conditioning, cFC occurs too late; after successful down-conditioning, it occurs on time.

DETAILED DESCRIPTION OF THE INVENTION

Figure 1:
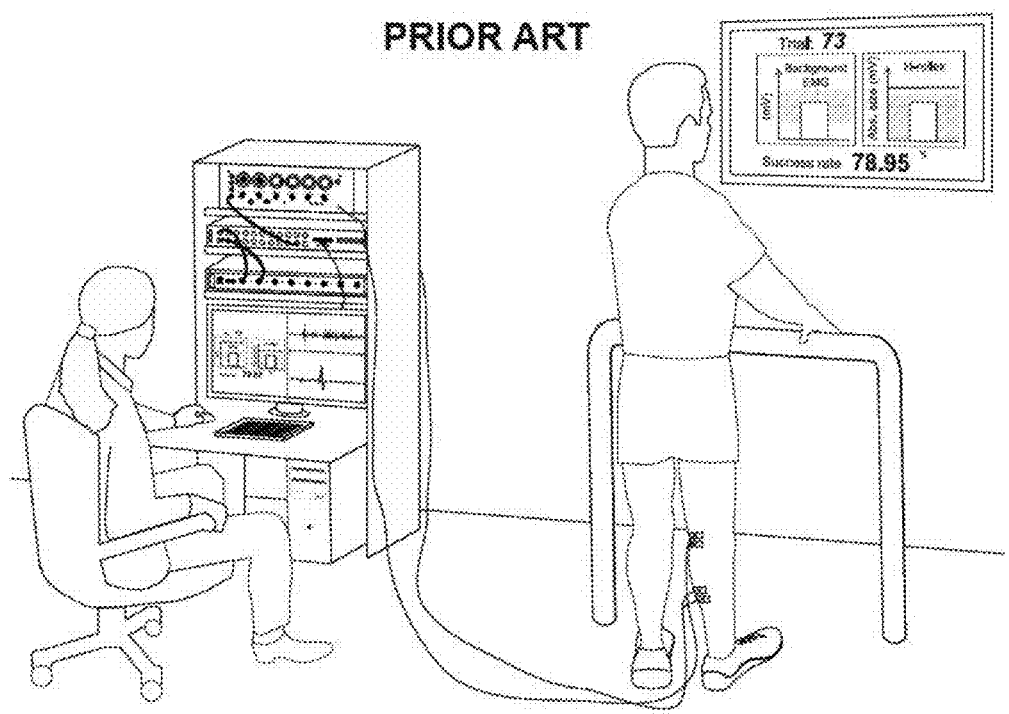
FIG. 1 is an illustration of a standard laboratory set-up for operant conditioning of the soleus H-reflex.

In a general sense, the present invention provides new and useful methods, devices, and systems for use in the field of neurological rehabilitation. More particularly, the present invention provides methods, devices, and systems for restoring and/or improving nervous system function of a subject, whether the subject is a patient in need of neurological rehabilitation or a person interested in improving or maximizing his neurological function in a particular area. Therefore, in certain aspects, the present invention provides new and useful methods, devices, and systems for use by those who wish to improve and/or reach their optimal performance potential with respect to their central nervous system (CNS) sensorimotor and/or cognitive functions (e.g., athletic performance, memory skills, etc.).

As used herein, the term "subject" refers to an animal or human in need of neurological rehabilitation or desirous of improving, restoring, and/or both improving and restoring a nervous system function or aspect thereof. A subject can be of any age or gender. Further, a subject can include a patient of neurological rehabilitation, or a person having normal nervous system function.

As used herein, the term "nervous system function" refers to any function related to the nervous system of a subject. The nervous system function can be important or secondary. The nervous system function can be, without limitation, any CNS sensorimotor function or cognitive function. Examples of nervous system functions can include, without limitation, locomotion (walking), reach-and-grasp functions, withdrawal responses, hand control, arm control, attention, perception, emotional control, reading, arithmetic, memory, and other cognitive or nervous system functions, including those not specifically named herein but understood by those of ordinary skill in the art to be cognitive or nervous system functions.

Method of Improving Nervous System Function

In one aspect, the present invention provides a method for restoring or improving nervous system function of a subject. This method involves the steps of (i) providing an operant conditioning protocol effective to produce targeted neural plasticity (TNP) in a primary targeted central nervous system (CNS) pathway of a subject; and (ii) administering the operant conditioning protocol to the subject under conditions effective to elicit TNP in the primary targeted CNS pathway and to elicit generalized neural plasticity (GNP) in one or more other CNS pathway. The elicitation of the GNP in the one or more other CNS pathway serves to restore or improve a nervous system function of the subject.

In one embodiment, the method of the present invention can be implemented by using a device or system of the present invention as disclosed herein.

In one embodiment of this method, the operant conditioning protocol is self-administered by the subject.

Suitable operant conditioning protocols for use in the method of the present invention are as described herein. In various embodiments, the operant conditioning protocol is designed to down-condition hyperactive reflexes in the subject, up-condition hypoactive reflexes in the subject, and/or up-condition or down-condition other CNS pathways.

As provided herein, the method of the present invention provides operant conditioning protocols effective to produce targeted neural plasticity (TNP) in a primary targeted CNS pathway of a subject. Suitable primary targeted CNS pathways of the subject can include, without limitation, a monosynaptic pathway of a spinal stretch reflex, a monosynaptic pathway of a Hoffman reflex (H-reflex), a spinal pathway of cutaneous reflexes, a corticospinal tract, a reciprocal thalamocortical pathway that produces electroencephalographic (EEG) sensorimotor rhythms (SMRs), and other CNS pathways, including other CNS pathways not specifically named herein but understood to be CNS pathways by those of ordinary skill in the art.

As provided herein, in accordance with various embodiments of the method of the present invention, operant conditioning protocols are administered to a subject under conditions effective to elicit TNP in the primary targeted CNS pathway and to elicit generalized neural plasticity in one or more other CNS pathway. As used herein, the one or more other CNS pathway can include, without limitation, other spinal reflex pathways, other corticospinal connections, intracerebral connections, cortical-subcortical pathways, and any other CNS pathway, including other CNS pathways not specifically named herein but understood to be CNS pathways by those of ordinary skill in the art.

As set forth herein, the method is for restoring and/or improving nervous system function in a subject. In various embodiments, the restored and/or improved nervous system function includes, without limitation, locomotion (walking), a withdrawal response, hand control, arm control, reach-and-grasp control, attention, perception, emotional control, reading, arithmetic, memory, and other cognitive functions.

In further aspects, the present invention provides various other embodiments of a method for restoring and/or improving nervous system function in a subject. As provided in the examples contained herein, in accordance with aspects of the present invention, an operant conditioning protocol produces targeted neural plasticity (TNP) in the CNS that leads to additional beneficial plasticity at many other CNS sites, and can thereby greatly improve all aspects of a complex behavior that has been impaired by trauma or disease. For example, in people in whom an incomplete spinal cord injury has produced spasticity and foot-drop in one leg that greatly impairs walking, operant conditioning that weakens a particular overactive reflex pathway in that leg leads to widespread plasticity that improves all aspects of walking, including muscle activity in the opposite leg (Thompson et al., 2013). That is, the benefits of operant conditioning of a single reflex pathway go far beyond the direct effects of the TNP in the targeted reflex pathway itself: the entire behavior of walking becomes faster and more symmetrical (e.g., limping disappears and muscles on both sides behave more effectively). In sum, the TNP produced by an appropriate reflex operant conditioning protocol focused on a correctly chosen single CNS pathway triggers widespread beneficial plasticity that improves walking in general. This profound and widespread impact was not expected, much less demonstrated, until the present invention. Thus, the present invention provides novel methods for rehabilitation, since the same method could be applied to other CNS pathways, and could improve a broad spectrum of important CNS functions.

Now that this effect has been discovered, it can be understood as a result of the continual adaptive processes occurring in the CNS. Without intending to be limited by any particular theory, as behaviors (i.e., CNS functions) are performed, the CNS is continually evaluating the results and producing plasticity at one or more of the many CNS sites involved in the behavior so as to optimize performance. By producing appropriate plasticity at one of these sites (i.e., targeted neural plasticity (TNP)), a properly selected operant conditioning protocol changes the ongoing interactive process of multisite adaptive plasticity and enables the CNS to arrive at a superior solution; that is, it enables the CNS to adjust many of the involved sites (i.e., to produce generalized neural plasticity (GNP)) so as to improve the behavior to a level superior to that obtained prior to exposure to the operant conditioning protocol.

In one embodiment of the method of the present invention, there is provided a method with well-defined steps, as well as a particular exemplary embodiment of the method. The purpose of this method is to improve the performance of complex nervous system functions. As discussed herein, to do this, it uses operant conditioning protocols to produce targeted neural plasticity (TNP) in specific central nervous system (CNS) pathways that have important roles in the functions. This TNP triggers further plasticity in other CNS pathways important to the functions and thereby leads to widespread improvement in the functions. This method can be applied to improve basic motor skills such as walking or reach-and-grasp, as well as higher-level CNS functions (e.g., attention, perception, emotional control, memory, reading, and arithmetic). Furthermore, it can be used for rehabilitation (i.e., to restore functions that have been impaired by injury or disease) or to enhance specific functions beyond their normal level in people without disabilities.

In an embodiment of the present invention, the method exposes the individual to an operant conditioning protocol in which the response being conditioned is produced by a specific and well-defined CNS pathway that also contributes to much more complex and important CNS behaviors such as walking. The protocol produces TNP in the pathway; that is, it changes the pathway, and as a result it also affects the complex behaviors (e.g., walking) that use the pathway. Surprisingly, by affecting another behavior such as walking, the TNP in the target pathway also triggers widespread plasticity in other pathways that contribute to that other behavior. In an individual with function impaired by CNS trauma or disease, induction of this widespread plasticity can improve an impaired behavior toward normal. In a healthy individual without CNS trauma or disease, induction of TNP plasticity by an appropriately selected protocol may improve a behavior beyond its normal range.

Table 1 includes a listing of various examples of how the method of the present invention can be applied, as follows:

TABLE 1

Examples of Applications of the Method

| CNS pathway targeted for plasticity | Behavioral context of the operant conditioning protocol | CNS output that determine reward/no reward | CNS function that is improved |
|---|---|---|---|
| Monosynaptic pathway of the spinal stretch reflex or H-reflex | Steady-state muscle activity (EMG) or a specific phase of locomotion | Spinal stretch reflexes or H-reflexes | Walking |
| Spinal pathway of cutaneous reflexes | Steady-state EMG | EMG responses to cutaneous nerve stimulation | Walking; Withdrawal responses |
| Corticospinal tract | Steady-state EMG | First EMG response to electrical (rats) or magnetic (humans) stimulation of cortex | Walking; Hand/arm control |
| Reciprocal thalamocortical pathways that produce EEG sensorimotor rhythms (SMRs) | Controlling EEG SMR amplitudes to move a cursor to a target on a screen | Mean SMR amplitude before or during the period of cursor control to a specific target | Reach-and-grasp; Other discrete skilled actions |

As shown in Table 1, the method, device, and system of the present invention can be used in numerous applications. In view of the present disclosure and teachings herein, those applications are understood by those of ordinary skill in the art. For example, with regard to cutaneous reflexes, these are known to consist of several different latency components, just like stretch reflexes. Thus, the earliest response is not necessarily the most functional or meaningful in motor control.

Devices and Systems for Improving Nervous System Function

In another aspect, the present invention provides a device for restoring or improving nervous system function of a subject. The device comprises a nerve stimulation-electromyographic recording component and a controller for operating the nerve stimulation-electromyographic recording component in accordance with an operant conditioning protocol. The nerve stimulation-electromyographic recording component comprises a nerve stimulator for stimulating a primary targeted central nervous system (CNS) pathway in a subject, at least one stimulating electrode array in functional communication with the nerve stimulator and adapted for topical contact with the subject, and at least one electromyographic (EMG) recording electrode array for recording EMG data of the subject produced in response to the stimulation of the primary targeted CNS pathway. As mentioned, the device also comprises a controller for operating the nerve stimulation-electromyographic recording component in accordance with an operant conditioning protocol. The operant conditioning protocol is effective to produce targeted neural plasticity (TNP) in the primary targeted CNS pathway of the subject.

In another aspect, the present invention provides a system for restoring or improving nervous system function of a subject. The system comprises the device of the present invention in functional communication and/or in functional combination with any other apparatus, component, device, or system that enables the functioning of the device for use by a subject. The device of the present invention, which comprises the main part of any system of the present invention, is described in more detail herein and particularly below.

In various embodiments, a suitable nerve stimulator of the device comprises an apparatus for providing a current or voltage pulse of selectable polarity, duration, and strength at externally triggered times through a pair of skin-mounted electrodes selected from a stimulating electrode array. In a particular embodiment, the at least one stimulating electrode array comprises one or more possible pairs of stimulating electrodes.

In various embodiments, the at least one EMG recording electrode array comprises one or more possible pairs of EMG recording electrode arrays.

In accordance with various embodiments of the device of the present invention, suitable operant conditioning protocols can include those that are effective to also elicit generalized neural plasticity (GNP) in one or more other CNS pathway, where the elicitation of the GNP in the one or more other CNS pathway serves to restore or improve a nervous system function of the subject.

As set forth herein, the device of the present invention also includes a controller for operating the nerve stimulation-electromyographic recording component of the device. In one embodiment, the controller comprises a computer processor and corresponding software effective to perform the operant conditioning protocol on the subject. As set forth herein and below, the software for use with the device and the controller of the device can have various attributes and functions in the operation of the device, system, and methods of the present invention.

In one embodiment, the software evaluates all possible pairs of stimulating electrodes to choose the most effective pair. For example, the software can operate so that the pair of stimulating electrodes elicits a soleus muscle response (M-wave) at the lowest stimulus level and does not elicit a response in another muscle (e.g., tibialis anterior).

In another embodiment, the software evaluates all possible pairs of soleus muscle recording electrodes to choose the most effective pair. For example, the software can operate so that the pair of soleus muscle recording electrodes detects a soleus muscle response at the lowest stimulus level.

In another embodiment, the software automatically adjusts stimulus strength as needed to maintain the target M wave. For example, the software can automatically adjust stimulus strength between trial blocks to maintain the target M wave.

In another embodiment, the software automatically adjusts the amplitude criterion for reward as needed to maintain an appropriate reward frequency. For example, the software can automatically adjust the amplitude criterion for reward between trial blocks to maintain an appropriate reward frequency.

In yet another embodiment, the software notifies the subject and/or a therapist via the internet of any problem in EMG recording, in the responses obtained, or in other aspects of operation, and provides instructions and oversight for resolving the problem. For example, the software can notify the subject and/or a therapist via the internet of any problem in EMG recording (e.g., non-EMG artifacts), in the responses obtained, or in other aspects of operation, and provides instructions and oversight for resolving the problem.

In various embodiments, the controller comprises a monitoring component effective to provide real-time feedback to the subject during performance of the operant conditioning protocol. Suitable monitoring components can include any monitoring component that is effective to provide visual real-time feedback, audio real-time feedback, both visual and audio real-time feedback, and/or other sensory real-time feedback to the subject.

In various embodiments, the controller is in communication with the nerve stimulation-electromyographic recording component. Communication between the controller and the nerve stimulation-electromyographic recording component can be via a wireless or wired functional connection.

In other embodiments, the controller provides the subject with complete and appropriately illustrated instructions for donning and doffing the device, parameterizing the operant conditioning protocol, performing the operant conditioning protocol, and handling associated details selected from the group consisting of data storage, Internet-based interaction with a therapist, and the like.

In certain embodiments, the device of the present invention further comprises a wearable placement component for positioning the at least one stimulating electrode array at a stimulation target area of the subject and/or for positioning the at least one EMG recording electrode array at an EMG recording target area of the subject. Suitable examples of wearable placement components can include, without limitation, any wrap device (e.g., a leg wrap, a wrist wrap, a shoulder wrap, a back wrap, etc.), a garment, or other means for holding the device in place for use by the subject.

With regard to placement of the stimulating electrode arrays, in one embodiment, the stimulation target area of the subject is an area of the skin of the subject suitable for stimulating the primary targeted CNS pathway in the subject.

With regard to the placement of the EMG recording electrode arrays, in one embodiment, the EMG recording target area of the subject is an area of the skin of the subject suitable for facilitating the recording of the recording EMG data of the subject produced in response to the stimulation of the primary targeted CNS pathway.

In certain other embodiments, the device of the present invention further comprises a wireless communication device for receiving, displaying, storing, and/or analyzing data generated by the controller. Suitable examples of a wireless communication device as used herein can include, without limitation, a computer, a computer tablet, a personal digital assistant (PDA), a mobile phone, a portable digital media player, a personal eyewear apparatus for receiving and displaying data generated by the controller, and a dedicated digital device for receiving and displaying the data generated by the controller. In particular examples, the personal eyewear apparatus can include in-eye digital lenses (contact lenses with digital monitoring functionality) or a wearable computer with an optical head-mounted display (OHMD) such as the product known as Google Glass. Other wearable wireless communication devices can be those that can be mounted on a garment or other item worn by the subject (e.g., a visor of a hat so that the subject can view a digital display).

The present invention also includes connected or wired (i.e., not wireless) communication devices as a means for receiving, displaying, storing, and/or analyzing data generated by the controller. Therefore, the present invention contemplates connected or wired wearable communication devices that correspond with any of the above wearable wireless communication devices, with the difference being the wired connection between the controller and the wearable communication device.

In various embodiments, the present invention provides a device for improving nervous system function of a subject that is usable by the subject in a home or other setting without expert assistance or oversight. The device is effective for performing the various embodiments of the method of the present invention as described herein. In a particular embodiment, the device is effective in performing a particular method of the present invention for improving walking in people in whom walking has been impaired by a spinal cord injury or other neuromuscular trauma or disease. Prior to the present invention, such a method required a cumbersome complex arrangement of laboratory equipment (see FIG. 1) and the continuous active involvement and oversight of a highly skilled technician with specialized knowledge and experience in clinical neurophysiology or closely related disciplines. In contrast, the device of the present invention is a highly compact, portable, and fully automated unit that can be used by a subject independently in the home without the involvement of an expert (see, e.g., FIG. 2). The therapist can oversee progress via the Internet and through occasional formal evaluations in the clinic. The device eliminates the complex cumbersome laboratory apparatus and accomplishes through novel software algorithms the essential steps that previously required the continual involvement and adjustments of a highly trained expert. It enables an affected individual to apply an appropriate reflex operant conditioning protocol to produce targeted neural plasticity (TNP) that triggers widespread plasticity that restores more normal walking.

In various embodiments, the device of the present invention translates the effective new therapeutic method already validated in rats and in humans with spinal cord injuries into a clinically and commercially practical system that can significantly enhance recovery of function beyond that achievable with current neurorehabilitation regimens. Furthermore, this unit is readily usable by patients on a daily basis without close oversight, which allows frequent use with minimal demand on therapist time and effort. Device operation and results can be monitored periodically through the Internet. The embodiment described here targets the soleus H-reflex. The device can also target other spinal cord reflexes or brain-spinal cord connections.

Figure 2:
FIG. 2 is an illustration one embodiment of a spinal reflex operant conditioning system as disclosed herein.

As shown in FIG. 1, the prior art methods and devices required a cumbersome laboratory system and setup. By way of contrast, as shown in FIG. 2, the present invention provides a device 16 that is compact, portable, and fully automated. FIG. 2 illustrates the device's physical simplicity and its ability to function without expert involvement or oversight. Its key hardware and software components and their functions are described herein in more detail.

In various embodiments, to accomplish its essential functions, the device incorporates automated capacities for: selection of stimulation and recording sites; derivation of reflex recruitment curves; selection and ongoing adjustment of stimulus parameters with absolute safeguards against inappropriate stimulation; selection and ongoing adjustment of operant conditioning criteria; artifact detection and correction; data collection and storage; Internet-based transmission of data and operating parameters; and periodic or ad hoc two-way Internet-based interaction with a clinic-based therapist for data monitoring or parameter adjustment. This device consists of hardware and software.

In various embodiments of the device, the hardware includes: a programmable nerve stimulation-EMG (electromyographic) recording (NS-EMG) component that can be mounted (e.g., via a wrap) at a given place on the body (e.g., calf and knee) (see FIGS. 2 and 3); and a video screen (i.e., the interface). These two parts can communicate via telemetry (i.e., the cloud).

In a particular embodiment, the programmable NS-EMG component has various component parts, including, without limitation, those described as follows: A flexible comfortable wrap that can be fixed in place at a specific orientation over the knee and calf can be used. It can be adjustable to limb size. Embedded in the wrap can be an array of small stimulating electrodes that contact the skin in the popliteal fossa (i.e., behind the knee) (see FIG. 3). Embedded in the wrap can also be a ground electrode that contacts the skin of the knee cap (i.e., the front of the knee) (see FIG. 3). Embedded in the wrap can also be an array of small EMG recording electrodes that contact the skin over the soleus muscle (i.e., middle and lower posterior calf) (see FIG. 3). Embedded in the wrap can further be an array of small EMG recording electrodes that contact the skin over the tibialis anterior muscle (i.e., middle anterior calf) (see FIG. 3). An externally programmable bipolar nerve stimulator capable of delivering 1-50 mA, 0.1-2.0 ms pulses at intervals of 100 ms or more and approved for human use can be embedded in the device. An electronic multi-channel switch that connects a programmable set of stimulation electrodes to the positive and negative outputs of the nerve stimulator can be embedded in the device. An electronic multi-channel switch that connects a programmable set of recording and stimulating electrodes to the EMG amplifier can be embedded in the device. A multichannel EMG amplifier and digitizer, connected to the multichannel recording/stimulation switch, can be embedded in the device. This amplifier and digitizer are able to record from 64 electrodes (i.e., 32 bipolar channels). The amplifier and digitizer are able to record the ongoing EMG activity, the stimulation artifact, and the subsequent EMG response. A wireless two-way low-power interface (IEEE 802.11 b/g/n, Bluetooth 4.0) can be used to connect the device to the cloud and the user interface. The QOS settings of the wireless interface ensure a round-trip time of <200 ms, which allows the NS-EMG device to function properly.

In some embodiments, initial configuration of the NS-EMG device is either performed through paring the NS-EMG device with an iOS or Android device over a Bluetooth ad-hoc connection or through connecting to a Windows or Macintosh PC via a USB connection. The iOS, Android, Windows or Macintosh devices run proprietary software that configures the connection of the NS-EMG device to the cloud. This includes the WiFi SSID name and WEP, WPA, WPA2, WPA-personal, WPA-enterprise keys for multiple wireless IEEE 802.11 b/g/n networks. Once the NS-EMG device is fully configured it will connect automatically to any wireless network that was previously configured.

In some embodiments, the NS-EMG device functions together with a leg wrap, disposable electrodes, a programmable controller, a video screen, a cloud service and a wireless network (see FIGS. 2-6).

In some embodiments, the NS-EMG device can be distributed over the counter with supplies (i.e., 200 disposable electrode array sets), a manual and video instructions.

The NS-EMG device can operate autonomously or under supervision of a clinician or therapist in a clinic or through a subscription service.

The programmable controller and video screen component performs the following functions without human intervention or guidance:

It provides information and instructions to the device user regarding each step in the protocol. The video display shows the subject how to don the device and initiate operation; and it leads the subject through each step in the selection of recording and stimulating electrodes, the selection of the background EMG range, the derivation of the M-wave and H-reflex recruitment curves, and the performances of control and conditioned H-reflex trials.

In various embodiments, it selects the stimulating and recording electrode pairs. Using a short (e.g., 1-50 mA, 1-msec) square-wave stimulus pulse, it begins at a sub-threshold stimulation level and cycles through the possible stimulating electrodes (and both polarities of each pair) at a brisk rate (e.g., 0.5 Hz) while monitoring all recording electrode pairs; and it raises stimulus amplitude in small increments until a threshold M-wave is reliably obtained. The stimulating electrode pair and polarity that elicits and the recording electrode pair that detects, respectively, that response are selected to be used thenceforth.

In various aspects, it is understood that, if the stimulation rate is too high, postactivation depression of the H-reflex will get in the way to detect an optimum stimulus location. In the active muscle (i.e., with background EMG activity), 0.5 Hz stimulation won't induce postactivation depression. In a resting muscle, it will (postactivation depression can be observed up to 0.1 Hz).

In various embodiments, it determines the EMG level that corresponds to a maximum voluntary contraction (MVC) (measured as absolute value of EMG (i.e., rectified EMG)). It asks the subject to produce a MVC for about 3 sec, and repeats this request several (e.g., 3) times at a minimum interval of about 1 min. In various embodiments, a longer interval than 1 min can be used to obtain MVC correctly. However, 1 min can be viewed as the minimum in various embodiments. It determines the average absolute value for the middle 2 sec of each MVC and averages the highest three values of the four MVCs to determine the MVC. The background EMG level required during H-reflex trials is defined as a fixed range in percent (e.g., 10-20%) of this MVC (or, alternatively, as a specific range in µV).

In various embodiments, it identifies the time windows in the EMG following nerve stimulation that reflect, respectively, the effective stimulus strength (Window A) (e.g., the M-wave) and the strength of the response of the nervous system pathway to be modified (Window B) (e.g., the H-reflex). It defines the M-wave window from EMG responses to several times (e.g., twice) M-threshold stimulation at a rate of about 0.5 Hz. It defines the H-reflex window based on the standard H-reflex latency range and the responses to 1-2× M-threshold stimulation at 0.2 Hz in the presence of a correct background EMG level (as defined above and herein).

In various embodiments, it elicits a Window A/Window B recruitment curve. It obtains this M-wave/H-reflex recruitment curve in the presence of the required background EMG level. It begins below M-wave threshold and gradually increases the stimulus to Mmax, stimulating about 4 times at each stimulus level at a rate of 0.2 Hz. Based on the results, it selects a target M-wave (i.e., Window A) amplitude and a corresponding stimulus level for the H-reflex trials.

In various embodiments, in initial sessions (i.e., Baseline sessions) it uses the chosen stimulating and recording electrodes and the selected stimulus amplitude to conduct several (e.g., 3) control H-reflex elicitation blocks (e.g., 75 trials each). In each trial, the H-reflex is elicited after the subject maintains background EMG in the required range for several sec.

During these blocks of control trials, it provides visual (and/or other sensory) feedback to the user of current EMG background level versus the required range. For example, a graph on the video screen displays the current EMG level as a vertical bar superimposed on the required background range; the bar is green when it falls in the range and red when it does not.

In various embodiments, it may also provide more complex sensory feedback, such as in the context of a game that actively engages the subject and motivates the subject to use the device more often and for more trials, and thereby augments the production of generalized neural plasticity (GNP) and its beneficial effects on CNS function. Thus, it may complement and enhance conventional rehabilitation and training regimens by motivating activities that engage the most relevant nervous system pathways.

In various embodiments, it stores complete EMG data for each stimulation (i.e., each trial).

In various embodiments, throughout the baseline sessions, it periodically adjusts the stimulus level to maintain the target M-wave amplitude.

In various embodiments, it calculates average Window A (M-wave) and Window B (H-reflex) amplitudes for all baseline sessions. The distribution of H-reflex amplitudes is used to determine the initial reward criterion value for the conditioning sessions (e.g., if the goal is to make the H-reflex larger, the criterion might be set so that the largest 60% of the H-reflexes satisfy it).

In various embodiments, in subsequent H-reflex conditioning sessions, it uses the chosen stimulating and recording electrodes to conduct a block of about 20 control H-reflex elicitation trials followed by three blocks (e.g., 75 trials each) of conditioning H-reflex trials. In each control or conditioning trial, the H-reflex is elicited after the subject maintains background EMG in the required range for several sec.

In addition, in various embodiments, in conditioning trials only, the subject is provided immediate feedback indicating whether the H-reflex size satisfied the criterion value. A second graph on the video screen displays H-reflex size as a vertical bar and the current H-reflex criterion value as a superimposed range (i.e., above or below a given value). The bar is green when H-reflex size falls in the range and red when it does not.

In various embodiments, throughout the conditioning sessions, it periodically adjusts stimulus amplitude to maintain the target M-wave amplitude.

In various embodiments, between the trial blocks of the conditioning sessions, it adjusts the H-reflex amplitude criterion to maintain an appropriate reward probability (e.g., 60%).

In various embodiments, it continues to store all trial data for later analysis and summary.

It interacts via the Internet with a remote site for data transfer. Following each session and/or whenever requested remotely by a therapist, it sends complete data and all current parameters to the therapist via the Internet. In addition, it accepts changes in parameters (e.g., target reward probability) from the therapist.

Exemplary Embodiments of Devices and Systems for Improving Nervous System Function For illustrative purposes, provided below are descriptions of exemplary embodiments of devices and systems for improving nervous system function as provided by the present invention and as performed in accordance with methods of the present invention. More particularly, below are further descriptions of the exemplary embodiments of the present invention as shown in FIGS. 2-6.

For context, reference is made to FIG. 1, which is an illustration of a standard laboratory set-up for operant conditioning of the soleus H-reflex. As shown in FIG. 1, in standard operant conditioning of the soleus H-reflex, a trained therapist is needed to assist with the process. Further, large equipment set-ups are used during the process, and the subject is hooked to such equipment during the process.

By way of the contrast, as shown in FIG. 2, the device, system, and/or method of the present invention do not require large equipment or a trained therapist to be present during the procedure. FIG. 2 is an illustration one embodiment of a spinal reflex operant conditioning system as disclosed herein. As described above, no therapist or system operator is necessary. The electronics and the computer shown in the rack in FIG. 1 are incorporated into the pocket shown in the lower leg wrap (16), and they communicate via telemetry with a cloud service and the user interface (i.e., the monitor on the table in front of the subject).

Figure 3:
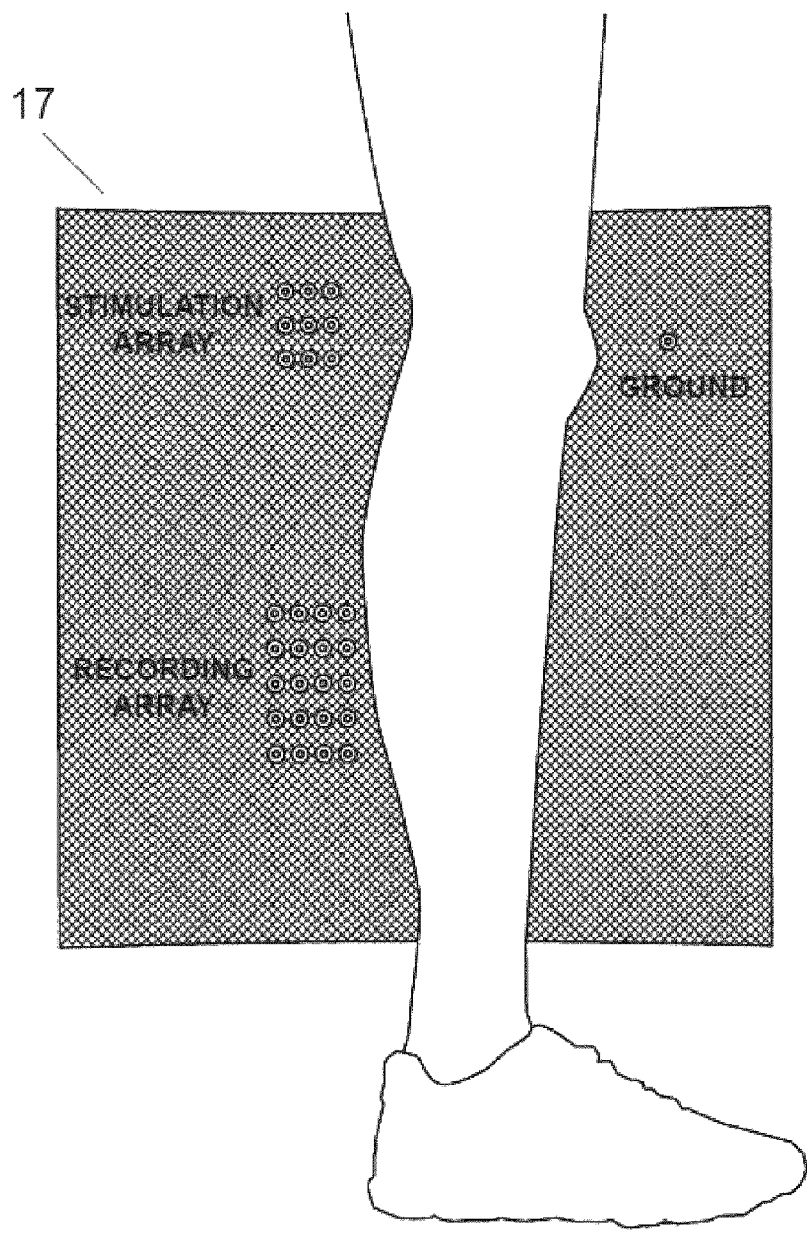
FIG. 3 is an illustration of one embodiment of a device as disclosed herein. In this embodiment, device 17 is in the form of a leg wrap and is shown in its open position to show the popliteal simulating electrode array ("stimulation array") and the soleus muscle recording electrode array ("recording array"). A "ground" electrode is also illustrated.

As shown in FIG. 3, in one embodiment, device 17 is in the form of a leg wrap. As shown in FIG. 3, the leg wrap includes a popliteal simulating electrode array ("stimulation array") and a soleus muscle recording electrode array ("recording array"), as well as a "ground" electrode.

Figure 4:
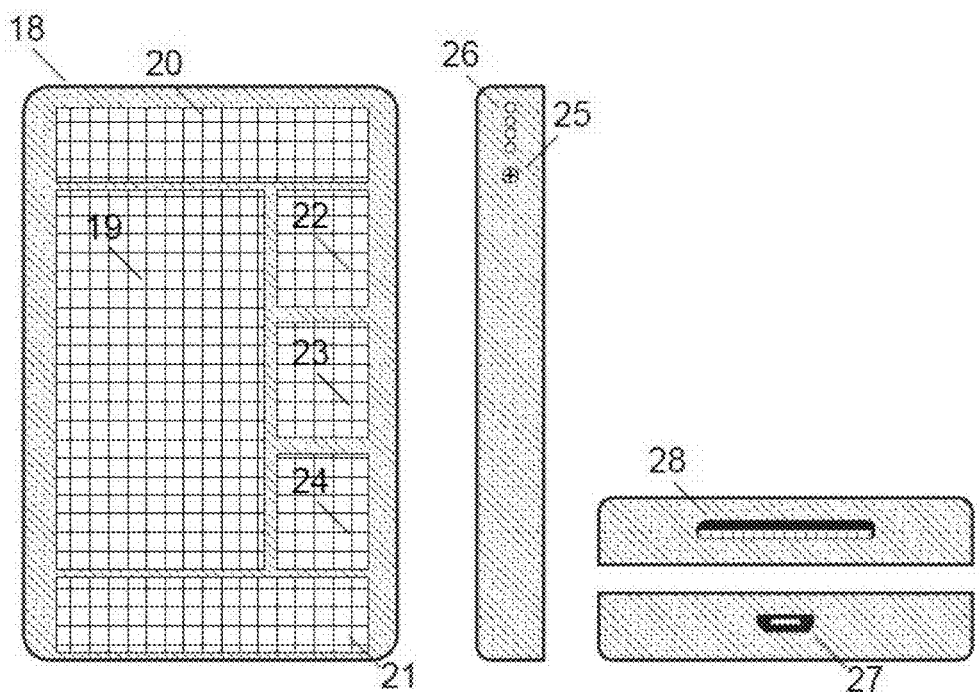
FIG. 4 are illustrations of various views (i.e., face, side, top end, and bottom end views) of one embodiment of a nerve stimulation-electromyographic (NS-EMG) device 18 that comprises electronics that can be embedded in a pocket of a leg wrap embodiment of device 17 shown in FIG. 3. As shown, in various embodiments, NS-EMG device 18 can be encased in a waterproof (IPX-7) plastic case.

As shown in FIG. 4, in one embodiment, the present invention provides a nerve stimulation-electromyographic (NS-EMG) device that comprises electronics that can be embedded in a pocket of a leg wrap embodiment of device 17 shown in FIG. 3. As shown, in various embodiments, the NS-EMG device can be encased in a waterproof (IPX-7) plastic case 18.

Referring to FIG. 4, the NS-EMG device can contain the following: One 3.8V, 10 W lithium-polymer battery 19. One single stream 802.11-a/b/g/n antenna 20. One Bluetooth antenna 21. An analog processing unit 22 that records from and stimulate surface electrodes. The recording unit can consist of a programmable multichannel switch that selects a set of 64 electrodes, and an amplifier/digitizer that translates the selected channels into digital values. The stimulation unit can consist of a programmable multichannel switch that connects a set of electrodes to the positive and negative output of a nerve stimulator. The programmable human-rated nerve stimulator can output 1-50 mA 0.1-2.0 msec current pulses.

Referring again to FIG. 4, the NS-EMG device can contain the following: A digital processing unit 23 that processes the digitized signals and performs the stimulation paradigm where the digital processing unit communicates with the NS-EMG cloud service and the user interface over TCP/IP and HTML5 protocols. The NS-EMG device also can contain, as shown in FIG. 4, a digital storage unit 24 that stores the firmware and the recorded EMG data. The data is periodically uploaded to the NS-EMG cloud service. As shown in FIG. 4, the NS-EMG device can also be powered on and off via a push button 25 on the side of the plastic case. Pushing the button for more than 7 sec powers the device on/off. Pushing the button for less than 7 sec can show battery indicator lights 26. The NS-EMG device can be charged via a micro-USB port 27 on the bottom of the device. To ensure safety, operation of the device can be suspended while being charged. The NS-EMG device can be connected via a flat ribbon cable to the electrodes, as shown in FIG. 4 as drawing reference number 28.

Figure 5:
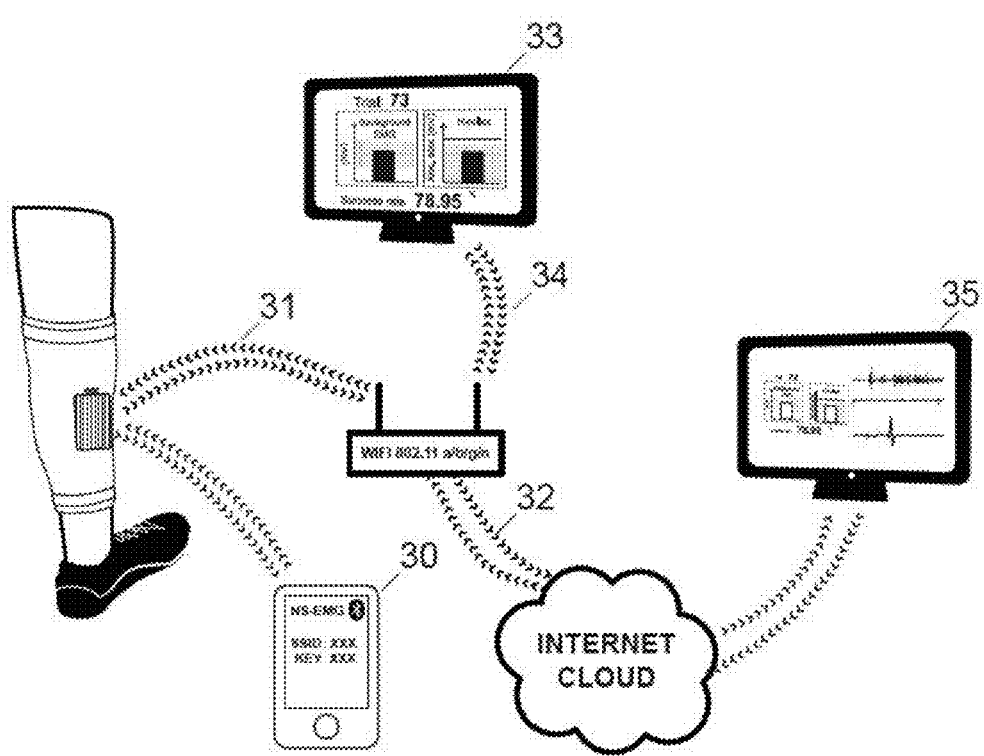
FIG. 5 is an illustration of one embodiment of a system comprising a device and implementing a method according to the present disclosure. This figure illustrates one embodiment of an initial set-up and subsequent communication of a device of the present disclosure with a cloud service and a user interface.

Referring to FIG. 5, in one embodiment, the present invention provides a device, method, and system that uses a portable device that communicates with the Internet via the cloud. FIG. 5 shows one embodiment of an initial set-up and subsequent communication of a device of the present disclosure with a cloud service and a user interface. As shown in FIG. 5, the NS-EMG device is initially configured over an ad-hoc paired Bluetooth Connection to an iOS, Android or Windows Phone compatible device (30). In this initial setup, the connection and user parameters are set. The connection parameters include the SSID and WEP/WPA/WPA2/WPA2-personal/WPA2-enterprise encryption keys for the 802.11-a/b/g/n networks to which the NS-EMG device connects. The user parameters include the username and password for the NS-EMG cloud service. The NS-EMG device automatically connects to any initially configured 802.11 a/b/g/n WiFi network (31). The NS-EMG device automatically registers with the NS-EMG cloud service upon connecting to a WiFi network (32). The user receives visual feedback on a HTML5 capable personal computer, tabled or phone (33). On this device the user connects to the NS-EMG cloud service using his username and password. The HTML5 interface is received from the cloud while the feedback values are directly received from the NS-EMG device, therefore ensuring the <200-ms real-time performance of the visual feedback (34). The clinician receives a summary of the training performance on a HTML5 capable personal computer, tablet, or phone (35). The interface to the clinician and all summary values are provided by the NS-EMG cloud service. All information is provided in a HIPAA compliant fashion.

Figure 6:
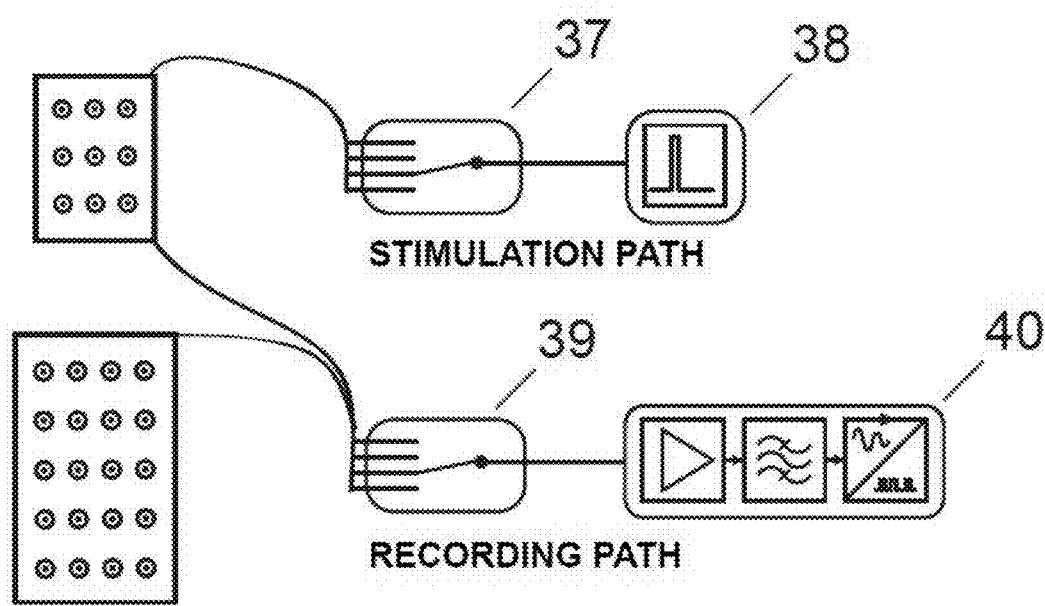
FIG. 6 is an illustration of one embodiment of a system comprising a device and implementing a method according to the present disclosure. This figure illustrates one embodiment of aspects of a system including stimulation and recording of the nerve stimulation and electromyographic (EMG) recording interfaces.

Referring to FIG. 6, in one embodiment there is provided a system including stimulation and recording of the nerve stimulation and electromyographic (EMG) recording interfaces. As shown in FIG. 6, the system can include a programmable multichannel switch that connects a subset of the stimulation electrodes to the positive and negative output of the nerve stimulator (37). The programmable nerve stimulator delivers single or trains of 1-50 mA current pulses that have a duration of about 1 ms and are triggered by the protocol (38). A programmable multichannel switch selects up to 64 of the stimulation and recording channels for the digitization step (39). The digitization step amplifies, band-pass filters and converts the signal into digital values at a rate of 2 kHz (40).

EXAMPLES

The following examples are intended to illustrate particular embodiments of the present invention, but are by no means intended to limit the scope of the present invention.

Example 1

Operant Conditioning of Rat Soleus H-Reflex Oppositely Affects Another H-Reflex and Changes Locomotor Kinematics

Overview

H-reflex conditioning is a model for studying the plasticity associated with a new motor skill. We are exploring its effects on other reflexes and on locomotion. Rats were implanted with EMG electrodes in both solei ($SOL_R$ and $SOL_L$) and right quadriceps ($QD_R$), and stimulating cuffs on both posterior tibial (PT) nerves and right posterior femoral nerve. When $SOL_R$ EMG remained in a defined range, $PT_R$ stimulation just above M-response threshold elicited the $SOL_R$ H-reflex. Analogous procedures elicited the $QD_R$ and $SOL_L$ H-reflexes. After a control period, each rat was exposed for 50 days to a protocol that rewarded $SOL_R$ H-reflexes that were above (HRup rats) or below (HRdown rats) a criterion.

HRup conditioning increased the $SOL_R$ H-reflex to 214 ($\pm$37SEM)% of control (P=0.02) and decreased the $QD_R$ H-reflex to 71($\pm$26)% (P=0.06). HRdown conditioning decreased the $SOL_R$ H-reflex to 69($\pm$2)% (P<0.001) and increased the $QD_R$ H-reflex to 121($\pm$7)% (P=0.02). These changes remained during locomotion. The $SOL_L$ H-reflex did not change. During the stance phase of locomotion, ankle plantarflexion increased in HRup rats and decreased in HRdown rats, hip extension did the opposite, and hip height did not change.

The plasticity that changes the $QD_R$ H-reflex and locomotor kinematics may be inevitable (i.e., reactive) due to the ubiquity of activity-dependent CNS plasticity, and/or necessary (i.e., compensatory) to preserve other behaviors (e.g., locomotion) that would otherwise be disturbed by the change in the $SOL_R$ H-reflex pathway. The changes in joint angles, coupled with the preservation of hip height, suggest that compensatory plasticity did occur.

The present study is the first effort to determine whether soleus H-reflex conditioning affects the H-reflex of a hindlimb muscle group (i.e., quadriceps (QD)) that operates about different joints (i.e., knee and hip rather than ankle), and whether it affects joint angles during locomotion. The data show that soleus H-reflex conditioning has a markedly different effect on the QD H-reflex and produces distinctive multi joint kinematic changes during locomotion. They indicate that the acquisition of an ostensibly simple new skill has an impact that extends beyond the new skill to affect a crucial older skill, and they raise important new questions.

Materials and Methods

Twenty-six male Sprague-Dawley rats (439($\pm$44 SD) g initially) were studied. All procedures satisfied the "Guide for the Care and Use of Laboratory Animals" (National Academy Press, Washington, D. C., 2011), and had been approved by the Wadsworth Center Institutional Animal Care and Use Committee. The methods have been fully described previously (Chen and Wolpaw 1995, 2002; Chen et al. 2005, 2006a, 2006b) and are summarized here.

Electrode Implantation

Under general anesthesia (ketamine HCl (80 mg/kg) and xylazine (10 mg/kg) (both i.p.) or sodium pentobarbital (60 mg/kg, i.p.), supplemented as needed) and aseptic conditions, each rat was implanted with chronic stimulating and recording electrodes in the right and left legs. To elicit H-reflexes in the right and left solei ($SOL_R$ and $SOL_L$), cuffs were placed on the right and left posterior tibial ($PT_R$ and $PT_L$) nerves just above the triceps surae branches. To elicit the H-reflex of the right quadriceps muscle group ($QD_R$), a similar cuff was placed on the right posterior division of the femoral ($PF_R$) nerve. To record $SOL_R$, $SOL_L$, and $QD_R$ EMG, a pair of stainless steel fine-wire electrodes was implanted in each. The soleus acts about the ankle joint to plantarflex the foot. The QD group comprises four muscles: vastus lateralis, medialis, and intermedialis, and rectus femoris. All four act about the knee to dorsiflex (i.e., extend) the calf, and the rectus femoris also acts about the hip to flex the thigh (i.e., to move it forward and up). The two $QD_R$ EMG electrodes were placed laterally (targeting vastus lateralis) and medially (targeting vastus medialis), respectively, so that their data would represent the entire QD muscle group. The Teflon-coated wires from all the electrodes passed subcutaneously to a connector on the skull.

After surgery, the rat was placed under a heating lamp and given an analgesic (Demerol, 0.2 mg, intramuscular). Once awake, it received a second dose of analgesic and was returned to its cage and allowed to eat and drink freely.

Experimental Design and $SOL_R$ H-reflex Conditioning

Data collection began at least 20 days after surgery and continued 24 hrs/day, 7 days/week for at least 70 days. During this period, the rat lived in a standard rat cage with a 40-cm flexible cable attached to the skull connector. The cable, which allowed the animal to move freely about the cage, connected to a commutator above the cage that connected to EMG amplifiers (gain 1000, bandwidth 100-1000 Hz) and the nerve-cuff stimulation units. The rat had free access to water and food, except that during H-reflex conditioning it received food mainly by performing the task described below. Animal well-being was carefully checked several times each day, and body weight was measured weekly. Laboratory lights were dimmed from 2100 to 0600 daily.

Stimulus delivery and data collection were controlled by a computer, which sampled (5 kHz) $SOL_R$, $SOL_L$, and $QD_R$ EMG continuously for the entire period of study. $SOL_R$ and $SOL_L$ H-reflexes were elicited simultaneously as follows. Whenever the absolute value (i.e., the full-wave rectified value) of background (i.e., ongoing) EMG in each muscle remained within a pre-defined range for a randomly varying 2.3-2.7 s period, the computer initiated a trial. In each trial, the computer stored the most recent 50 ms of EMG from all three muscles (i.e., the background EMG window), delivered simultaneous monophasic stimulus pulses through the cuffs on the $PT_R$ and $PT_L$ nerves, and stored the EMG from all muscles for another 100 ms. A comparable procedure elicited the $QD_R$ H-reflex by stimulating the $PF_R$ nerve whenever ongoing $QD_R$ EMG remained within a pre-defined range. Because SOL and QD H-reflex trials occurred only when the muscles satisfied their background EMG requirements, SOL and QD H-reflex trials seldom occurred in close proximity to each other.

Stimulus pulse amplitude and duration were initially set to produce a maximum H-reflex (and an M wave that was typically just above threshold) in the muscle served by the stimulated nerve. Pulse duration remained fixed (typically 0.5 ms). After each trial, pulse amplitude was adjusted automatically to maintain the M wave (i.e., average EMG amplitude in the M wave window (typically 2.0-5.0 ms in $SOL_R$ and $SOL_L$ and 1.5-4.5 ms in $QD_R$)) unchanged throughout data collection. (This ensured that the effective strength of the stimulus was stable throughout (Wolpaw 1987; Chen and Wolpaw 1995).) H-reflex size was defined as average EMG amplitude in the H-reflex window (typically 6-10 ms in $SOL_R$ and $SOL_L$ and 4.5-8.5 ms in $QD_R$) minus the muscle's average background EMG amplitude.

Under the control mode, the computer simply digitized and stored the EMG from each muscle for 100 ms following the stimulus. Under the $SOL_R$ up-conditioning (HRup) or down-conditioning (HRdown) mode, it also gave a food-pellet reward 200 ms after the $PT_R$ nerve stimulation if the average amplitude of $SOL_R$ EMG in the H-reflex window was above (HRup) or below (HRdown) a criterion. The criterion was set and adjusted daily as needed, so that the rat received an adequate amount of food (about 1000 pellets/day for a 500-gm rat).

Each rat was first studied under the control mode for about 20 days. It was then exposed to $SOL_R$ up-conditioning (HRup rats) or down-conditioning (HRdown rats) for 50 days. The last 10 control-mode days and the last 10 HRup or HRdown days (i.e., days 41-50 of conditioning) provided the data used to assess the impact of $SOL_R$ H-reflex conditioning on $SOL_R$, $QD_R$, and $SOL_L$ H-reflexes.

H-reflex and Kinematic Measurements During Treadmill Locomotion $SOL_R$ and $QD_R$ locomotor H-reflexes and right hindlimb kinematics were studied in two treadmill sessions, one during the control-mode days and one near the end of $SOL_R$ HRup or HRdown conditioning. Treadmill speed was the same in both sessions (typically 10-12 m/min), and EMG was continuously recorded (0.1-1.0 kHz bandpass), digitized (4.0 kHz), and stored. In each session, reflex data were collected for two 4-5 min periods. In one, the $PT_R$ nerve was stimulated to elicit the $SOL_R$ H-reflex, and in the other the $PF_R$ nerve was stimulated to elicit the $QD_R$ H-reflex. The nerve was stimulated when its muscle's EMG had remained in a specified high range for 200 ms. Thus the stimulus typically occurred in the later part of the right stance phase of the step cycle (about 100 ms past the middle of the muscle's locomotor burst). Stimulus amplitude was kept just above M-response threshold as described above. (H-reflex elicitation during stance meant that the reflex was measured at a time when its pathway is likely to affect locomotion.) In addition, the rat was videotaped (60 wraps/sec) from the right side during 4-5 min of treadmill walking without nerve stimulation.

Those trials for which $SOL_R$ or $QD_R$ EMG amplitude for the 20 ms immediately before the stimulus and M-response size satisfied specified criteria were averaged by triggering on the stimuli. Thus, the average pre-stimulus EMG amplitudes and M-response sizes were the same for the two treadmill sessions.

In video analysis, we identified the right stance-phase images and, using marks on the ankle, knee, and hip, calculated for the entire stance phase the average anterior hip angle (i.e., hip extension: the angle of the thigh to a horizontal line projecting forward from the hip), posterior knee angle, and anterior ankle angle (i.e., ankle plantarflexion), and the average height of the hip above the treadmill surface.

Statistical Analysis

The data fell into three categories. The first category consisted of $SOL_R$, $QD_R$, and $SOL_L$ H-reflexes elicited under the conditioning protocol, that is, throughout the day as the rat moved freely about its home cage. These are henceforth called "conditioning H-reflexes." The second category consisted of $SOL_R$ and $QD_R$ H-reflexes during the right stance phase of locomotion. These are called "locomotor H-reflexes." The third category consisted of average right stance-phase ankle, knee, and hip angles and average hip heights.

For each conditioning reflex, a paired t-test compared the average value for the last 10 days of $SOL_R$ HRup or HRdown conditioning to that for the last 10 control-mode days. For each locomotor reflex and joint angle and for hip height, a paired t-test compared the value for the second treadmill session to that for the first treadmill session.

Animal Perfusion and Anatomical Study

At the end of study, each rat received an overdose of sodium pentobarbital (i.p.) and was perfused through the heart. The EMG electrodes, nerve cuffs, and PT and PF nerves were examined and the SOL muscles of both sides were removed and weighed.

Results

Animals remained healthy and active throughout study. Body weight increased from 439(±44SD) g at implantation to 568(±54) g at perfusion. In all rats, postmortem examination found that the cuffs were in place and covered by connective tissue, and that the nerves were well preserved. $SOL_R$ and $SOL_L$ weights did not differ significantly, nor did they differ from those of 113 normal rats previously studied.

Effects of $SOL_R$ H-Reflex Conditioning on $SOL_R$, $QD_R$, and $SOL_L$ Conditioning H-reflexes To determine the final effect on each muscle's conditioning H-reflex size of $SOL_R$ HRup or HRdown conditioning, the muscle's average H-reflex size for the final 10 days of conditioning was calculated as percent of its initial H-reflex size (i.e., average of final 10 control-mode days). As in previous studies, successful $SOL_R$ H-reflex conditioning was defined as a change≥20% in the correct direction. By this criterion, $SOL_R$ H-reflex conditioning was successful in 9 HRup and 8 HRdown rats. In the remaining rats (4 HRup and 5 HRdown), the final $SOL_R$ H-reflex was within 20% of its initial value.

Figure 7:
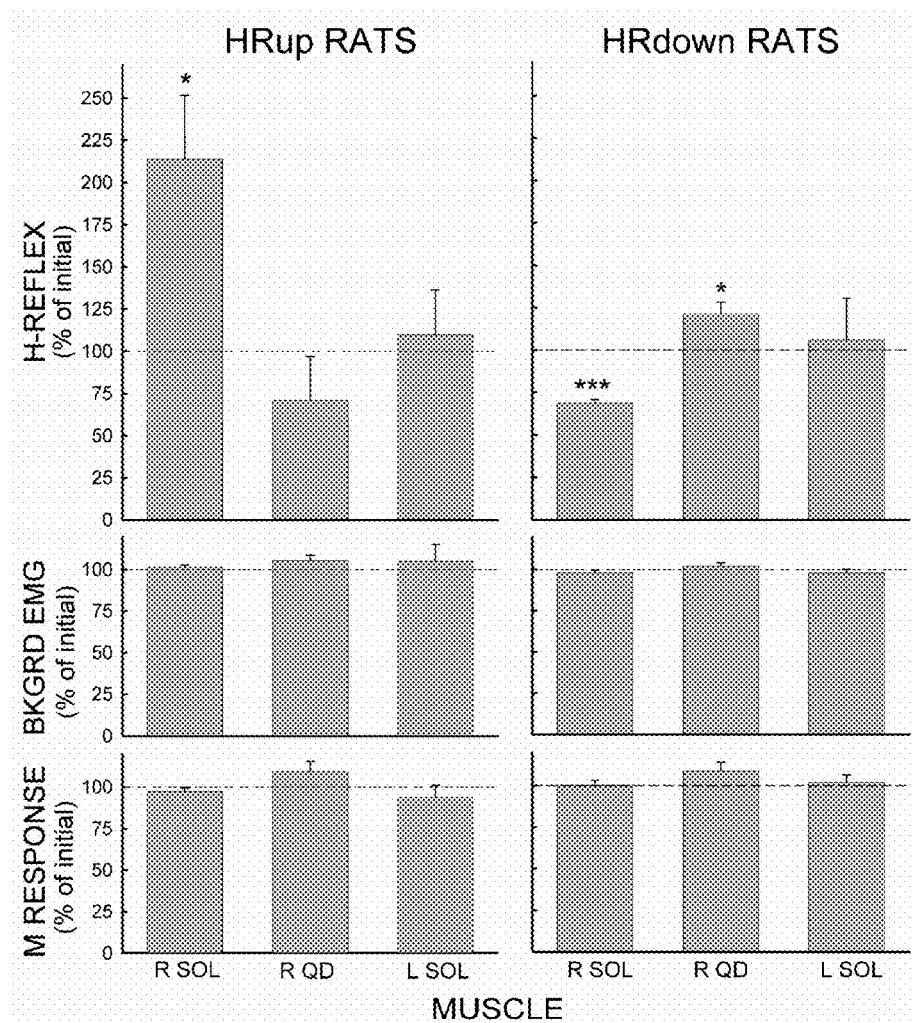
FIG. 7 are graphs showing effects of $SOL_R$ HRup and HRdown conditioning. Average final conditioning H-reflex, background EMG, and M wave (in % of their initial values) of $SOL_R$, $QD_R$, and $SOL_L$ for the successful HRup and HRdown rats. P values for difference from initial value by paired t-test are shown. *: P<0.05; ***: P<0.001.

FIG. 7 shows the average final values (±SEM) of $SOL_R$, $QD_R$, and $SOL_L$ H-reflexes, M waves, and background EMG in the successful HRup (left) and HRdown (right) rats in percent of their initial values. In accord with the goal of the conditioning protocol, the final $SOL_R$ H-reflex is markedly and significantly increased in HRup rats (P=0.02, paired t-test) and decreased in HRdown rats (P<0.001). In contrast, $SOL_R$ HRup or HRdown conditioning oppositely affected the $QD_R$ H-reflex: the final $QD_R$ H-reflex appears to be smaller in $SOL_R$ HRup rats (P=0.06), and is larger in $SOL_R$ HRdown rats (P=0.02). At the same time, neither $SOL_R$ HRup or HRdown conditioning has a noticeable effect on $SOL_L$ H-reflexes. In all rats, M waves and background EMG do not change.

Figure 8:
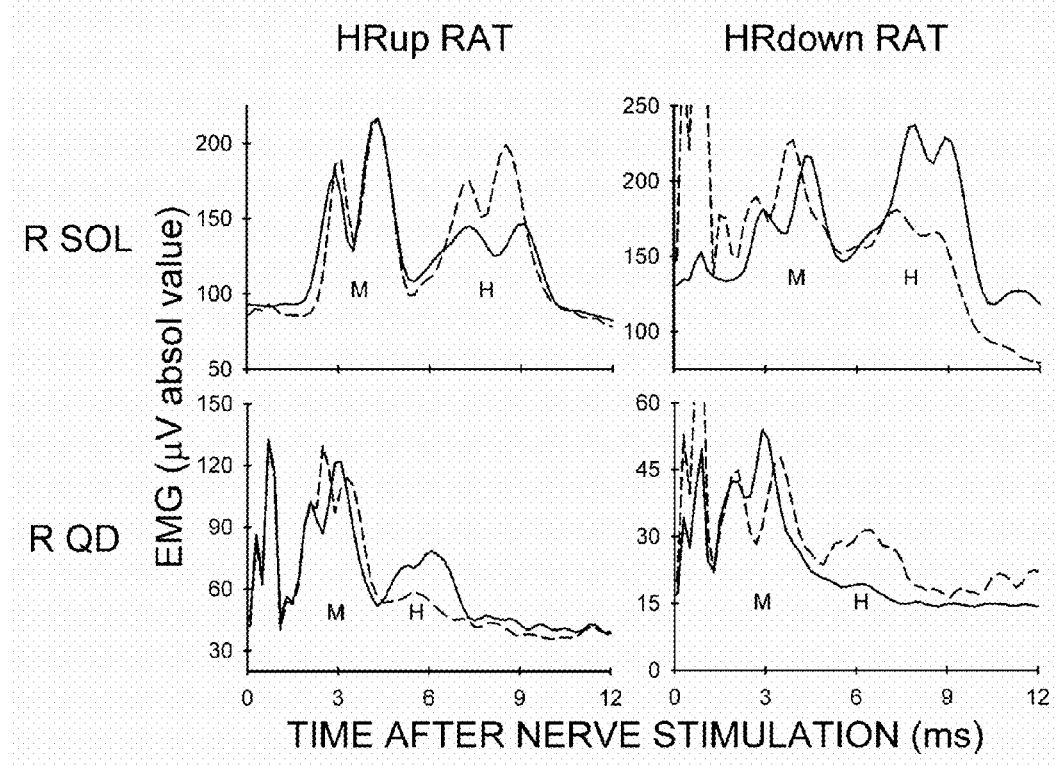
FIG. 8 are graphs showing effects of $SOL_R$ HRup and HRdown conditioning on the conditioning H-reflexes of representative rats. Average post-stimulus $SOL_R$ and $QD_R$ EMG for a control day (solid) and a day near the end of conditioning (dashed) for an HRup rat and an HRdown rat. After HRup conditioning the $SOL_R$ H-reflex is larger and the $QD_R$ H-reflex is smaller, while after HRdown conditioning the $SOL_R$ H-reflex is smaller and the $QD_R$ H-reflex is larger. Background EMG (EMG at time zero) and M-responses do not change. Peaks in the first 1-2 ms after stimulation are stimulus artifacts.

FIG. 8 shows initial and final $SOL_R$ and $QD_R$ H-reflexes for an HRup rat (left) and an HRdown rat (right). In the HRup rat, the $SOL_R$ H-reflex is markedly larger after conditioning while the $QD_R$ H-reflex is smaller. Conversely, in the HRdown rat, the $SOL_R$ H-reflex is much smaller after conditioning while the $QD_R$ H-reflex is larger.

Figure 9A:
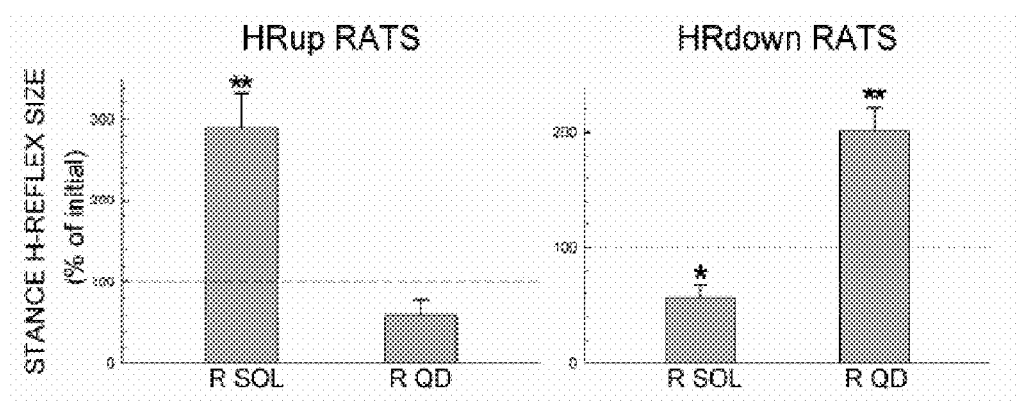
FIGS. 9A-9B are graphs showing effects of $SOL_R$ HRup and HRdown conditioning on the locomotor H-reflexes.

Effects of $SOL_R$ H-reflex Conditioning on $SOL_R$ and $QD_R$ Locomotor H-reflexes In 7 of the 9 successful HRup rats and 6 of the 8 successful HRdown rats, $SOL_R$ and $QD_R$ locomotor H-reflexes were also studied during the stance phase of locomotion before and after $SOL_R$ H-reflex conditioning. For these rats, FIG. 9A shows average final values (±SEM) of $SOL_R$ and $QD_R$ locomotor H-reflexes in percent of their initial control values. $SOL_R$ H-reflex conditioning has effects on the $SOL_R$ and $QD_R$ locomotor H-reflexes comparable to its effects on the conditioning H-reflexes. Indeed, the effects on the locomotor H-reflexes are even more prominent. Final $SOL_R$ locomotor H-reflexes are markedly and significantly increased in HRup rats (P=0.004) and decreased in HRdown rats (P=0.01). In contrast, $SOL_R$ HRup or HRdown conditioning has an opposite effect on the $QD_R$ locomotor H-reflex: it appears to be smaller in $SOL_R$ HRup rats (P=0.07) and is significantly larger in $SOL_R$ HRdown rats (P=0.004).

Figure 9B:
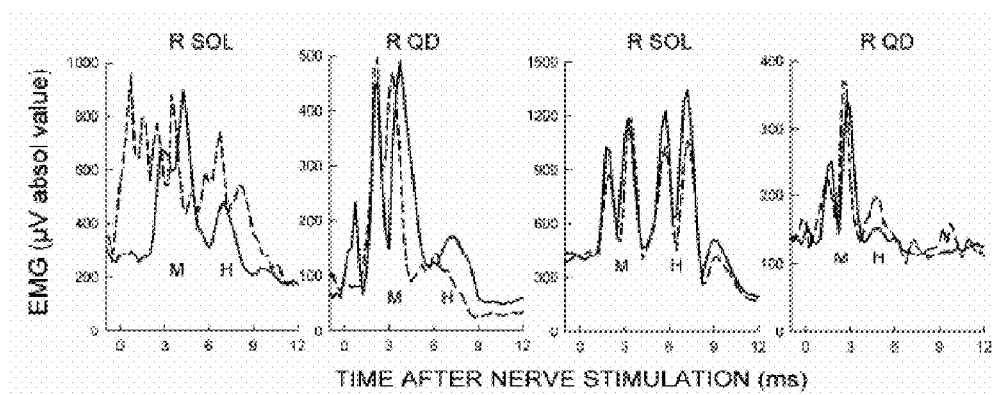

FIG. 9B shows initial and final $SOL_R$ and $QD_R$ locomotor H-reflexes for one HRup rat (left) and one HRdown rat (right). In the HRup rat, the $SOL_R$ H-reflex is markedly larger after conditioning while the $QD_R$ H-reflex is smaller. Conversely, in the HRdown rat, the $SOL_R$ H-reflex is smaller after conditioning while the $QD_R$ H-reflex is larger.

In the unsuccessful rats, final $SOL_R$ and $QD_R$ locomotor H-reflexes varied widely across animals. The $SOL_R$ locomotor H-reflex actually increased in 3 of the 5 unsuccessful HRdown rats, despite the fact that the $SOL_R$ conditioning H-reflex did not change in any of them. This result is consistent with an earlier study (Chen et al., 2005), and suggests that the lack of change in the conditioning H-reflex does not necessarily mean that conditioning has had no impact (Chen et al. (2005) for discussion).

Figure 10:
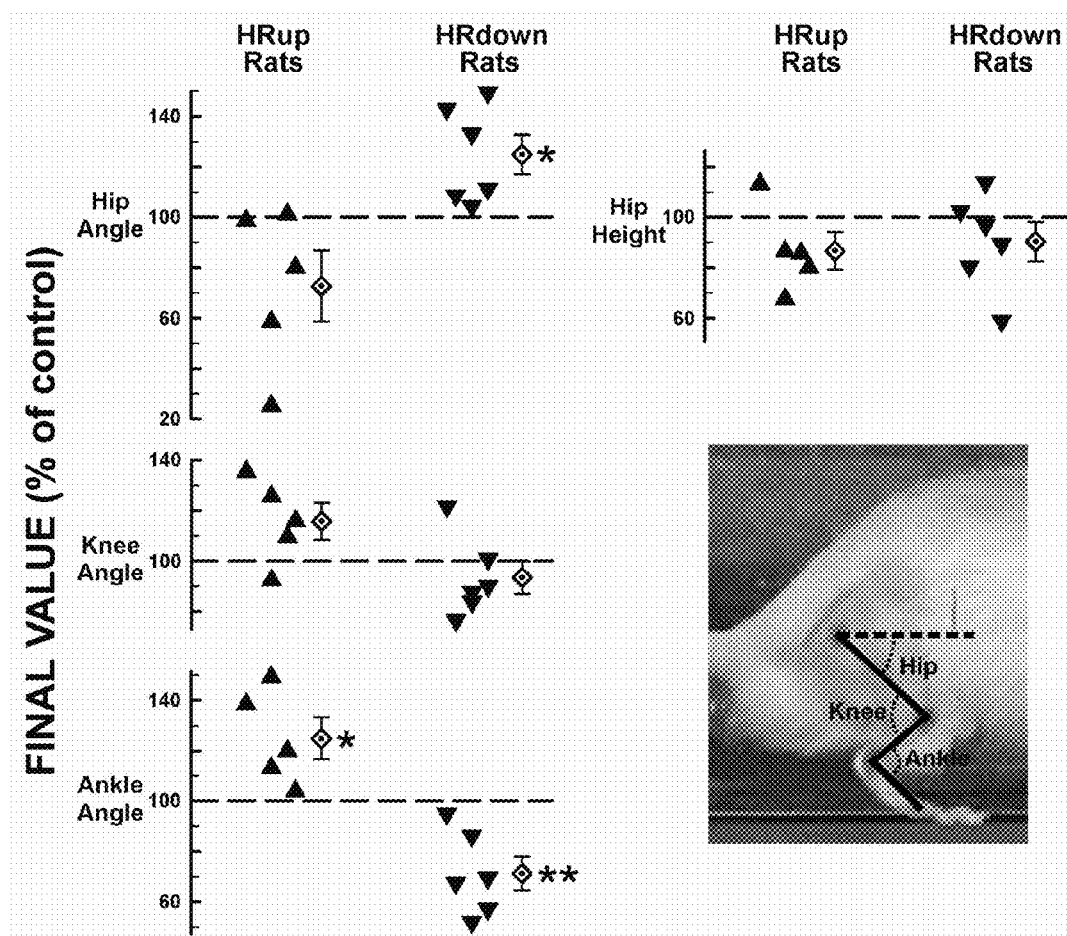
FIG. 10 are graphs showing Kinematic effects of $SOL_R$ HRup and HRdown conditioning. Individual and average (±SEM) final right stance-phase anterior ankle, posterior knee, and anterior hip angles (see inset), and hip height (in % of their initial values) for successful HRup (left) and HRdown (right) rats. The dashed horizontal line is parallel to the treadmill surface. P values for difference from the initial value by paired t-test are shown (*: P<0.05; **: P<0.01).

Effects of $SOL_R$ H-reflex Conditioning on Ankle, Knee, and Hip Angles and Hip Height In 5 successful HRup rats and 6 successful HRdown rats, average right ankle, knee, and hip angles and hip height during the stance phase of treadmill locomotion were determined before and after $SOL_R$ H-reflex conditioning. FIG. 10 shows, for each rat, the final values (±SEM) of these measures in percent of their initial values. In HRup rats, final anterior ankle angles were larger (P=0.04) (i.e., the ankle was more plantarflexed) and final anterior hip angles tended to be smaller (i.e., the hip was less extended) (P=0.13). In contrast, in HRdown rats, final ankle angles were smaller (P=0.008) and final hip angles were larger (P=0.03). Neither HRup nor HRdown conditioning significantly affected knee angle or hip height.

Discussion

Operant conditioning of the rat $SOL_R$ H-reflex has an opposite effect on the $QD_R$ H-reflex: in $SOL_R$ HRup rats the $QD_R$ H-reflex usually goes down, and in $SOL_R$ HRdown rats the $QD_R$ H-reflex goes up. These $QD_R$ H-reflex changes, like the $SOL_R$ changes, are still present, perhaps even greater, during locomotion. They occur despite the fact that they do not affect reward probability; the $QD_R$ H-reflex is elicited at different times from the $SOL_R$ H-reflex and is never associated with a reward. Nevertheless, it changes. Furthermore, $SOL_R$ H-reflex conditioning has effects on ankle angle during locomotion that are consistent with the $SOL_R$ H-reflex changes; and, in addition, it has opposite effects on hip angle, the etiology of which is not known at present.

The Plasticity Responsible for Change in the $Qd_R$ H-reflex

The $QD_R$ H-reflex is the earliest possible CNS-mediated QD response to the $PF_R$ nerve stimulus. Thus, the changes in $QD_R$ H-reflex size associated with $SOL_R$ H-reflex conditioning could reflect plasticity in the reflex pathway itself or plasticity in neurons or synapses that provide tonic input to the pathway, input that is there before the nerve stimulus. At present, evaluation of these two possibilities rests mainly on what is known about the change in the H-reflex that controls the reward (i.e., the conditioned H-reflex).

Physiological and anatomical studies (reviewed in Wolpaw and Chen 2009; Wolpaw 2010) indicate that the change in the reflex being conditioned (i.e., the $SOL_R$ H-reflex) is due mainly to plasticity in the motoneuron and/or the afferent pathway from the nerve stimulus, and that this plasticity is caused by change in corticospinal tract (CST) activity (which may pass through GABAergic interneurons in spinal laminae 6 and 7). For example, down-conditioning appears to be due mainly to a positive shift in motoneuron firing threshold (Carp and Wolpaw 1994). Furthermore, the change in the conditioned reflex is still evident when tonic inputs are greatly reduced or entirely eliminated (Wolpaw and Lee 1989). These findings suggest that the $QD_R$ H-reflex change reflects comparable plasticity in the $QD_R$ H-reflex pathway. This conclusion is supported by the fact that the $QD_R$ H-reflex change is still evident during locomotion, which would be expected to modify tonic inputs.

The Etiology of the Change in the $QD_R$ H-reflex and in Hip Angle

The plasticity that changes the $QD_R$ H-reflex or hip angle might occur in two ways. First, it might be an inevitable consequence of the fact that the capacity for activity-dependent plasticity is ubiquitous in the CNS. For example, the same CST activity that changes the $SOL_R$ H-reflex pathway might also produce an opposite change in the $QD_R$ H-reflex pathway. Such inverse effects on different muscles can occur with supraspinal lesions (e.g., Thompson et al. 2009b). Furthermore, the plasticity in the $SOL_R$ H-reflex pathway, by changing ongoing activity in intraspinal pathways, might itself induce plasticity in the $QD_R$ H-reflex. Comparable plasticity in spinal pathways that affect hip muscles might account for the change in hip angle. Plasticity created in such ways reflects the activity-dependent properties of individual neurons and synapses. Thus, its etiology is local, and it can be called "reactive" plasticity (Wolpaw 1997). A simple example of reactive plasticity is synaptic desensitization caused by increased synaptic input (e.g., Otis et al. 1996).

The second possible etiology of the $QD_R$ H-reflex change or the hip angle change is that it is adaptive, that it helps to compensate for the impact of $SOL_R$ H-reflex conditioning on other behaviors. Because the spinal cord is the final common pathway for many behaviors, the plasticity in the $SOL_R$ H-reflex pathway that increases reward probability affects other behaviors that also use this pathway. Indeed, $SOL_R$ H-reflex conditioning can be used to improve locomotion after a partial spinal cord injury (Chen et al. 2006b). In normal rats with normal locomotion, such side effects of H-reflex conditioning may induce additional activity-dependent plasticity that preserves normal locomotion (or other important behaviors). Chen et al. (2005) found that conditioning of the $SOL_R$ H-reflex changed SOL locomotor activity, but did not affect step-cycle length or symmetry, suggesting that other changes had preserved these major parameters of the step-cycle. This additional plasticity can be called "compensatory" (Wolpaw 1997). Unlike reactive plasticity, which originates locally, compensatory plasticity is induced and shaped by interactions between the CNS and the external world (Wolpaw 2010 for discussion).

The present kinematic results suggest that $SOL_R$ H-reflex conditioning does produce compensatory plasticity. $SOL_R$ H-reflex conditioning had effects on stance-phase ankle plantarflexion that are consistent with the $SOL_R$ H-reflex change: increase in HRup rats and decrease in HRdown rats. At the same time, it had opposite effects on hip extension: decrease in HRup rats and increase in HRdown rats. These opposite changes in hip angle appear to explain why hip height was not significantly changed despite the changes in ankle angle (i.e., FIG. 10).

A unilateral change in hip height during locomotion would presumably twist the thorax, which would probably have widespread short-term and long-term musculoskeletal effects. Nociceptive or other sensory inputs produced by this twisting might operantly condition compensatory plasticity that eliminates the twisting and preserves hip height. Thus, like step-cycle symmetry (Chen et al. 2005), hip-height symmetry during locomotion may be a functionally important parameter; and an intervention that disrupts it, such as $SOL_R$ H-reflex conditioning (which changes stance-phase foot plantarflexion), may induce compensatory plasticity that prevents the disruption. Whether the change in hip angle does reflect compensatory plasticity, whether reflex changes account for it, and why knee angle does not change instead (or in addition), are questions that will hopefully be elucidated by the comprehensive kinematic and reflex studies now underway (Liu et al. 2010).

Therapeutic Applications of Spinal Reflex Conditioning

H-reflex conditioning can improve locomotion in rats after a partial spinal cord injury (Chen et al. 2006b). Initial studies suggest that it can be effective in humans with spinal cord injuries, and they indicate that it requires only a small fraction of the conditioning trials normally used in animals (Pomerantz et al. 2010, Thompson et al. 2009a). The ability to target specific pathways could enable reflex conditioning protocols to supplement other therapeutic interventions such as locomotor training (Harkema et al. 2011). These protocols could be particularly useful when spinal cord regeneration becomes possible and methods are needed for guiding plasticity to produce a functionally effective spinal cord.

In the context of such therapeutic possibilities, the present results are both sobering and encouraging. They indicate the complexity of the effects that might accompany this new approach. At the same time, by suggesting that the plasticity induced by reflex conditioning may target the preservation (or restoration) of important functional parameters (e.g., hip height), they encourage further exploration of its therapeutic applications.

Conclusions

Soleus H-reflex conditioning also affects the H-reflex of the quadriceps muscle group, which operates about different joints, and it changes locomotor kinematics at both the ankle and the hip. The quadriceps H-reflex change remains evident during locomotion, and is probably due to plasticity in that H-reflex pathway. The change in hip angle is likely to reflect compensatory plasticity that preserves hip height in spite of the change in ankle angle. These results are striking evidence of the complex effects of acquiring an ostensibly simple skill. Their further study may illuminate the etiology and functional impact of the complex plasticity associated with new skills, and may guide development of new methods to improve function after trauma or disease.

Example 2

Operant Conditioning of a Spinal Reflex can Improve Locomotion after Spinal Cord Injury in Humans

Overview

Operant conditioning protocols can modify the activity of specific spinal cord pathways and can thereby affect behaviors that use these pathways. To explore the therapeutic application of these protocols, we studied the impact of down-conditioning the soleus H-reflex in people with impaired locomotion caused by chronic incomplete spinal cord injury. After a baseline period in which soleus H-reflex size was measured and locomotion was assessed, subjects completed either 30 H-reflex down-conditioning sessions (DC subjects) or 30 sessions in which the H-reflex was simply measured (Unconditioned (UC) subjects), and locomotion was reassessed. Over the 30 sessions, the soleus H-reflex decreased in two-thirds of the DC subjects (a success rate similar to that in normal subjects) and remained smaller several months later. In these subjects, locomotion became faster and more symmetrical, and the modulation of EMG activity across the step-cycle increased bilaterally. Furthermore, beginning about halfway through the conditioning sessions, all of these subjects commented spontaneously that they were walking faster and farther in their daily lives, and several noted less clonus, easier stepping, less arm weight-bearing, and/or other improvements. The H-reflex did not decrease in the other DC subjects or in any of the UC subjects; and their locomotion did not improve. These results suggest that reflex conditioning protocols can enhance recovery of function after incomplete spinal cord injuries and possibly in other disorders as well. Because they are able to target specific spinal pathways, these protocols could be designed to address each individual's particular deficits, and might thereby complement other rehabilitation methods.

The present study is the first effort to use spinal reflex conditioning to improve function in people with SCI. It focuses on people in whom a chronic incomplete SCI has produced a spastic gait disorder characterized by hyperreflexia and abnormal reflex modulation in ankle extensor muscles (Dietz and Sinkjaer, 2007; Nielsen et al., 2007). By down-conditioning the soleus H-reflex, the study sought to reduce these abnormalities, and to thereby improve the speed and symmetry of locomotion. The results are clear and encouraging. They suggest that operant conditioning protocols could provide a valuable new approach to restoring useful function after spinal cord injuries or in other neuromuscular disorders.

Materials and Methods

Subjects

The study participants were 13 ambulatory subjects (9 men and 4 women, ages 28-68 yrs, mean age 48.4

(±13.9SD)) (Table 2) who had suffered a spinal cord injury (SCI) 8 months to 50 years earlier that had impaired locomotion. All subjects gave informed consent for the study, which was reviewed and approved by the Institutional Review Board of Helen Hayes Hospital. A physiatrist (F.P.) determined each prospective subject's eligibility for the study. The inclusion criteria were: (1) a stable SCI-related motor deficit (>6 months after lesion); (2) ability to ambulate at least 10 m either with or without an assistive device (e.g., cane, crutches, or walker); (3) signs of spasticity (i.e., exaggerated H-reflexes, increased muscle tone, score≥1 on Modified Ashworth scale) and weak ankle dorsiflexion (i.e., manual dorsiflexor muscle strength at ankle<5) unilaterally or bilaterally; (4) a reasonable expectation that current medications would not change over the period of the study (e.g., an anti-spasticity medication such as baclofen, diazepam, or dantrolene); and (5) medical clearance to participate. The exclusion criteria were: (1) a lower motoneuron injury; (2) a known cardiac condition; (3) another medically unstable condition; (4) cognitive impairment; and/or (5) daily use of functional electrical stimulation to counteract foot drop. In the subjects who exhibited bilateral motor impairments, the soleus H-reflex of the more impaired leg was studied.

The subjects were randomly assigned (at a 2/1 ratio) to the Down-conditioning (DC) group (6 men and 3 women; ages 30-68 yrs, mean 48.2(±14.0SD) yrs; Subjects 1-9 in Table 2) or the Unconditioned (UC) group (3 men and 1 woman; ages 28-67 yrs, mean 48.8(±15.7) yrs); Subjects 10-13 in Table 2). The primary purpose of the UC group was to establish that H-reflex decrease was specific to the down-conditioning protocol.

TABLE 2

Profiles of Conditioning (DC) and Unconditioned (UC) Subjects.

| Group | Age | Gender | Cause | SCI Level | AIS | Yrs Post SCI |
|---|---|---|---|---|---|---|
| DC | 61 | M | NT | C7 | D | 10 |
| " | 68 | M | T | C3 | D | 2.5 |
| " | 37 | M | T | T6 | D | 0.7 |
| " | 39 | M | T | T11 | D | 1 |
| " | 30 | F | T | C5 | D | 7 |
| " | 34 | M | T | C2 | C | 1.5 |
| " | 51 | M | T | C5 | D | 0.8 |
| " | 65 | F | NT | T4 | D | 49 |
| " | 48 | F | NT | T7 | D | 5 |
| UC | 53 | M | T | C5 | D | 3 |
| " | 28 | M | T | C7 | C | 5.5 |
| " | 67 | F | NT | T4 | D | 50 |
| " | 48 | M | T | C3 | D | 0.8 |

M, Male; F, female; T, trauma; NT, non-trauma; SCI level, the highest spinal cord level that was damaged; AIS, American Spinal Injury Association Impairment Scale;, Cause: cause of spinal cord damage (T: trauma, NT: non-trauma).

Operant Conditioning of the Soleus H-reflex: Overview

The operant conditioning protocol for the human soleus H-reflex was originally developed in a study of neurologically normal subjects and is described in detail in Thompson et al. (2009). It is summarized here, with several minor modifications noted.

FIGS. 11A-11C summarize the protocol. After 1-3 preliminary sessions in which appropriate background EMG and M-wave criteria were defined, each subject completed 6 Baseline sessions and 30 Control (UC subjects) or Conditioning (DC subjects) sessions at a rate of 3 per week. Each session lasted about one hour and occurred within the same 2-h time window (to prevent the normal diurnal variation in reflex size from affecting the results (Wolpaw and Seegal, 1982; Chen and Wolpaw, 1994; Carp et al., 2006b; Lagerquist et al., 2006)). As FIG. 11B shows, in the 6 Baseline sessions of all subjects, and in the 30 Control and 2 Follow-up sessions of the UC subjects, 225 Control H-reflexes (in three 75-trial blocks) were elicited during standing. In these 225 Control trials there was no feedback to the subject regarding H-reflex size. In contrast, in the 30 Conditioning and 2 Follow-up sessions of the DC subjects, 20 Control H-reflexes were elicited, and then 225 Conditioned H-reflexes (in three 75-trial blocks) were elicited. In these 225 Conditioning trials, the subject was asked to decrease the H-reflex and was given immediate visual feedback after each stimulus (see below) to indicate whether the resulting H-reflex was smaller than a criterion value. Background EMG and M-wave size were kept stable throughout data collection.

Electrical Stimulation and EMG Recording

At the beginning of each session, EMG recording and stimulating electrodes were placed over the leg. EMG activity from soleus and its antagonist tibialis anterior (TA) was recorded with surface self-adhesive Ag—AgCl electrodes (2.2×3.5 cm, Vermed), amplified, band-pass filtered (10-1000 Hz), digitized (5,000 Hz), and stored. To elicit the H-reflex, the tibial nerve was stimulated in the popliteal fossa, using surface Ag—AgCl electrodes (2.2×2.2 cm for the cathode and 2.2×3.5 cm for the anode; Vermed) and a Grass S88 stimulator (with a CCU1 constant current unit and an SIU5 stimulus isolation unit; Astro-Med). The stimulating electrode pair was placed so as to minimize the H-reflex threshold and to avoid stimulating other nerves. This placement was accomplished by monitoring the EMG of soleus and TA and palpating other lower-leg muscles, such as the peroneal muscle group. To avoid session-to-session variability in electrode placement, their positions were mapped in relation to landmarks on the skin (e.g., scars or moles). The same individuals (AKT and BMA) placed the electrodes and conducted every session for every subject.

The soleus H-reflex was elicited by a 1-ms square stimulus pulse while the subject maintained a natural standing posture with hands resting on a horizontal bar at waist height and with stable levels of soleus and TA background EMG activity. The stimulus occurred after the subject had maintained rectified soleus and TA EMG activity within specified ranges for at least 2 s. Typically, the soleus range was 10-20% of a maximum voluntary contraction, and the TA range was 0-7 µV (i.e., resting level). The minimum interstimulus interval was 5 s.

Session Protocol

At the beginning of each session, an H-reflex/M-wave (H-M) recruitment curve was obtained. All H-reflex and M-wave measurements were in absolute value (i.e., equivalent to rectified EMG). Stimulus intensity was varied in increments of 1.25-2.50 mA from below soleus H-reflex threshold, to the maximum H-reflex ($H_{max}$), to an intensity just above that needed to elicit the maximum M-wave ($M_{max}$) (Kido et al., 2004b; Makihara et al., 2012). About 10 different intensities were used to obtain each recruitment curve. At each intensity, four EMG responses were averaged to measure the H-reflex and M-wave. The stimulus amplitude used for the subsequent H-reflex trials fell on the rising phase of the H-reflex recruitment curve and typically produced an M-wave just above threshold. In each subject, this M-wave size was maintained for the H-reflex trials of all the sessions.

In the Baseline and Control sessions (i.e., FIG. 11B), the H-M recruitment curve was followed by three 75-trial blocks of Control trials, in which the subject was not asked to change the H-reflex and was not given visual feedback as to H-reflex size (see Visual Feedback). In the Conditioning sessions (i.e., FIG. 11B), the H-M recruitment curve was followed by a 20-trial block of Control trials identical to those of the Baseline or Control sessions; and this block was followed by three 75-trial blocks of Conditioning trials, in which the subject was asked to decrease H-reflex size and was provided with immediate visual feedback that indicated his or her success in doing so (see below).

Visual Feedback

The visual feedback screens for Control and Conditioning trials have been described in detail previously (Thompson et al., 2009) and are illustrated in FIG. 11C. Briefly, the screen could present two graphs, one for soleus background EMG activity and one for H-reflex size. In Control trials, only the background EMG graph was shown: if the subject kept the height of the vertical bar (i.e., soleus background EMG activity level (in absolute value)) in the specified range for 2 s, and at least 5 s had passed since the last stimulus, a stimulus pulse elicited the H-reflex and M-wave. In Conditioning trials, the background EMG graph was shown and, in addition, the H-reflex size graph was shown. This graph constantly showed a heavy horizontal line indicating the subject's average H-reflex size for the 6 Baseline Sessions and a shaded area that indicated the H-reflex size range that satisfied the current down-conditioning criterion value. Two hundred msec after the stimulus, a vertical bar reflecting H-reflex size appeared. The bar was green (indicating success) when the H-reflex fell within the shaded area (i.e., was below the criterion value), and the bar was red (indicating failure) when the H-reflex size was not below the criterion value. In addition, the current success rate (i.e., the percent of the trials of the current 75-trial block that were successful) was shown below the graph and was updated after each trial. Thus, for each Control trial, the visual feedback simply helped the subject maintain the required pre-stimulus background EMG activity. In contrast, for each Conditioning trial, the visual feedback also informed the subject as to whether s/he had succeeded in producing an H-reflex small enough to satisfy the size criterion, and it showed the success rate for the current block of trials.

In each Conditioning session, the criterion value for the first block of 75 Conditioning trials was based on the immediately preceding block of 20 Control trials, and the criterion values for the second and third blocks of Conditioning trials were based on the H-reflexes of the immediately preceding block of 75 Conditioning trials. The criterion was selected so that if H-reflex values for the new block were similar to those for the previous block, 50-60% of the trials would be successful (Chen and Wolpaw, 1995). For each block, the subject earned a modest extra monetary reward when the success rate exceeded 50%. (See (Thompson et al., 2009) for full details.)

Analysis of Conditioned and Control H-Reflexes

For each session of each subject, we determined the average H-reflex size for the 225 trials of the three 75-trial blocks (FIG. 11B). This value is called the Conditioned H-reflex size (regardless of whether the session is from a Conditioning (DC) subject or an Unconditioned (UC) subject). In addition, for each session of each subject, we determined the average H-reflex size for 20 Control trials. This value is called the Control H-reflex size. For the 6 Baseline sessions of all subjects and the 30 Control sessions of the UC subjects, these 20 Control trials were the first 20 trials of the first 75-trial block. For the 30 Conditioning sessions and the Follow-up sessions of the DC subjects, these 20 Control trials were elicited prior to the three 75-trial blocks of Conditioning trials, as indicated in FIG. 11B. H-reflex size was defined as average absolute value of soleus EMG (i.e., equivalent to rectified EMG) in the H-reflex window (typically 30-45 ms after the stimulus) minus average absolute value of soleus background EMG.

To determine for each subject whether the Conditioned H-reflex size changed significantly over the 30 Conditioning or Control sessions, the average H-reflexes for the 225 trials of the three 75-trial blocks of the final 6 sessions (i.e., sessions 25-30) were compared to the average H-reflexes for the 225 trials of the three 75-trial blocks of the 6 baseline sessions by unpaired t test (two-tailed). To determine for each subject the final Conditioned H-reflex size, the average H-reflexes for the 225 trials of the three 75-trial blocks of the final 3 sessions (i.e., sessions 28-30) were averaged, and the result was expressed in percentage of the average H-reflex for the 225 trials of the three 75-trial blocks of the 6 Baseline sessions. (Thus, a value of 100% indicated no change.) To determine for each subject the final Control H-reflex size, the average H-reflexes for the 20 Control trials of sessions 28-30 were averaged, and the result was expressed in percentage of the average H-reflex for the 20 Control trials of the 6 Baseline sessions.

To assess the stability of soleus $M_{max}$, soleus M-wave size in Control and Conditioning trials, and soleus and tibialis anterior (TA) background EMG levels, a repeated measures ANOVA was applied to the mean values across successive 6-session blocks beginning with the 6 Baseline sessions. Soleus $M_{max}$, soleus M-wave size during H-reflex elicitation, and soleus and TA background EMG levels remained stable across all the sessions in both the Conditioning (DC) and Unconditioned (UC) groups ($p>0.33$ for all of these measures in both groups, one-way repeated measures ANOVA). These results confirmed the stability of EMG recording and nerve stimulation conditions in this study, and thus supported the validity of the methodology.

Assessment of Locomotion

Locomotion was assessed before and after the 30 Conditioning or Control sessions. These assessments occurred on non-session days. First, the subject was asked to walk 10 m overground at a comfortable speed three times, and the average walking time was determined.

Then, locomotor symmetry, EMG activity, and H-reflex modulation were measured. For these measurements during locomotion, any subject who wore an ankle foot orthosis was asked to remove it. Surface EMG was recorded from the soleus, TA, vastus lateralis (VL), and biceps femoris (BF) muscles of both legs. Footswitch cells inserted between the subject's shoe and foot detected foot contact (typically, heel or toe contact). For locomotor H-reflex measurement, single 1-ms square-pulse stimuli were delivered at different points in the step cycle to evaluate phase-dependent H-reflex modulation (Capaday and Stein, 1986; Stein and Capaday, 1988; Ethier et al., 2003; Kido et al., 2004b). The stimulus interval was set to be long enough to have at least one full unstimulated step cycle between successive stimuli.

Those subjects who were able to walk on a treadmill for several minutes with a consistent stepping rhythm did so twice at a comfortable speed: once without H-reflex elicitation and once while tibial nerve stimulation elicited the soleus H-reflex. Subjects who were not able to walk on the treadmill repeated 10-m overground walking without stimulation until at least 50 steps were obtained. They then repeated 10-m overground walking with H-reflex elicitation until at least 50 stimulated steps were obtained. During these measurements, the subjects took sitting breaks as often as needed. The data were assessed as described below, and the locomotor measurements obtained before and after the 30 Conditioning or Control sessions were compared.

For analysis of locomotor EMG activity, the complete step cycle was divided into 12 bins of equal duration (Kido et al., 2004a; Makihara et al., 2012). For the muscles of the conditioned leg, the step cycle went from the conditioned leg's foot contact (cFC) to the next cFC; for the muscles of the contralateral (i.e., nonconditioned) leg, the step cycle went from the nonconditioned leg's foot contact (nFC) to the next nFC. For each muscle of each subject, the average rectified EMG amplitude in each of the 12 bins was determined and expressed in percent of the amplitude in the bin with the highest amplitude. The degree to which each muscle's activity was modulated during locomotion was determined by calculating its Modulation Index (MI) in percent as: 100×[(highest bin amplitude−lowest bin amplitude)/highest bin amplitude] (Zehr and Kido, 2001; Zehr and Loadman, 2012). Thus, an MI of 0% indicated that a muscle did not modulate its activity at all over the step cycle.

To assess gait quality, we examined step-cycle symmetry (i.e., the ratio of the time between the nonconditioned leg's foot contact (nFC) and the conditioned leg's foot contact (cFC) to the time between cFC and nFC). A ratio of 1 indicates a symmetrical gait.

Spontaneous Subject Comments

Over the three months of the study, the subjects were not asked about the current state of their motor function or whether their disabilities had changed in any way. Nevertheless, many volunteered comments when they came in for sessions. We kept a record of these spontaneous comments and when they were first made. They fall into distinct categories and tell a clear story both in their nature and in their timing. Thus, they are presented as a unique and important component of the results.

Results

All 13 subjects completed the 6 Baseline sessions and 30 Conditioning or Control sessions. In each subject, soleus $M_{max}$, soleus M-wave size in Control and Conditioning trials, and soleus and tibialis anterior (TA) background EMG levels remained stable across all the sessions. The DC and UC groups did not differ significantly in soleus and TA background EMG levels (p=0.90 and 0.81 by two-way repeated measures ANOVA, respectively), M-wave sizes (p=0.71), or Baseline H-reflex sizes (p=0.11).

The results comprise three categories of data: Conditioned and Control H-reflex sizes over the course of the sessions; locomotor speed, symmetry, EMG activity, and H-reflex modulation before and after the 30 Conditioning or Control sessions; and the spontaneous comments of the subjects over the course of the sessions. These three data sets are described here.

H-Reflex Size

Figures 12A, 12B, 12C:
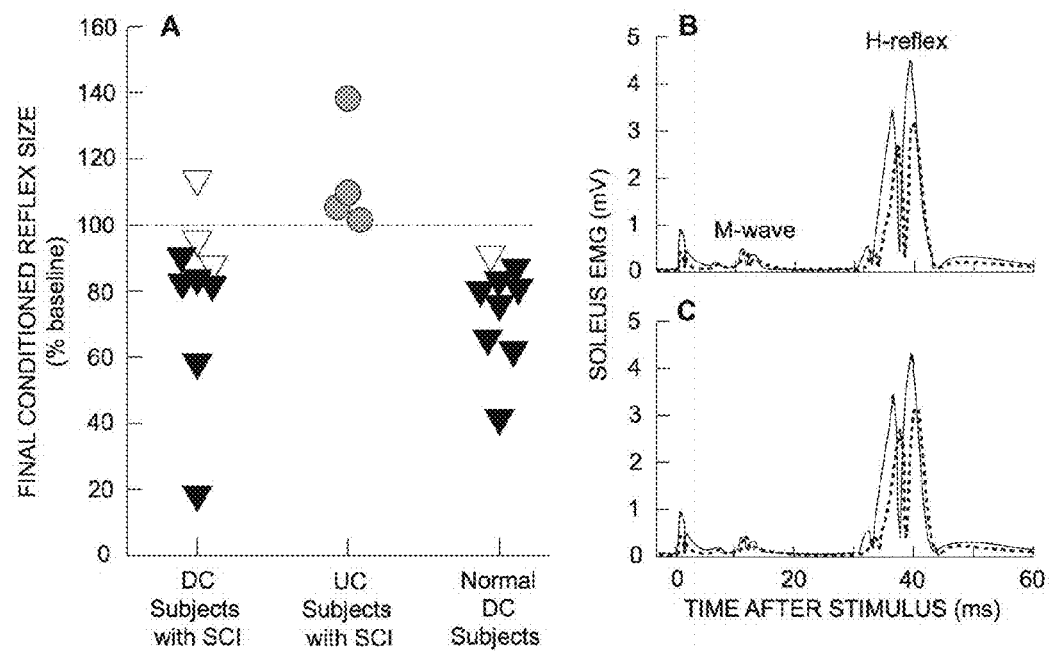
FIGS. 12A-12C are graphs showing H-reflexes from a successful DC subject during the Baseline period and at the end of the 30 Conditioning sessions.

FIG. 12A shows the final Conditioned H-reflex sizes of the DC subjects, the UC subjects, and, for comparison, the normal DC subjects of Thompson et al. (2009). The filled triangles represent the DC subjects in whom down-conditioning was successful (i.e., the average Conditioned H-reflexes for Conditioning sessions 25-30 were significantly less than those for the 6 Baseline sessions). In the other DC subjects (open triangles), the H-reflex did not change significantly. The success rate for the subjects with SCI (i.e., 6/9 or 67%) is slightly, but not significantly, less than that for neurologically normal subjects (i.e., 8/9 or 89%) (Thompson et al., 2009) or for normal monkeys, rats, and mice (i.e., 75-80%) (Wolpaw et al., 1983; Wolpaw, 1987; Chen and Wolpaw, 1995; Carp et al., 2006a). In contrast, the Conditioned H-reflex did not decrease significantly in any of the UC subjects; and the DC and UC groups differed significantly in final H-reflex size (p=0.025 by unpaired t test). Thus, H-reflex decrease was specific to the DC group. Indeed, it should be noted that the UC group as a whole showed a slight but significant increase in the Conditioned H-reflex (to 116(±7SE)% of baseline; p=0.05 by paired t test). This may have been a nonspecific effect of continued exposure over 30 sessions to the baseline protocol of standing, providing soleus background EMG, and having the H-reflex elicited.

As noted in our previous study of H-reflex conditioning in normal subjects (Thompson et al., 2009), successful DC subjects reported that, in the first 4-5 Conditioning sessions, they tried different strategies for decreasing the H-reflex, identified an effective strategy, and then used it in subsequent Conditioning trials. Their reported techniques were comparable to those of normal subjects (Table 2 of Thompson et al., 2009) (e.g., meditation, anticipating stimulus occurrence).

FIGS. 12B and 12C show H-reflexes from a successful DC subject during the Baseline period (solid) and at the end of the 30 Conditioning sessions (dashed). FIG. 12B illustrates the change in the Conditioned H-reflex (i.e., the H-reflex for the three 75-trial blocks in which the subject was asked to decrease the H-reflex and was provided with immediate feedback as to whether the reflex satisfied the size criterion). FIG. 12C illustrates the change in the Control H-reflex (i.e., the H-reflex for the first 20 trials of each Conditioning session in which the subject was not asked to decrease the H-reflex and was not provided with feedback as to reflex size). Both the Conditioned and Control H-reflexes are smaller after down-conditioning. Background soleus EMG level and M-wave size do not change.

Figures 13A, 13B, 13C, 13D, 13E, 13F:
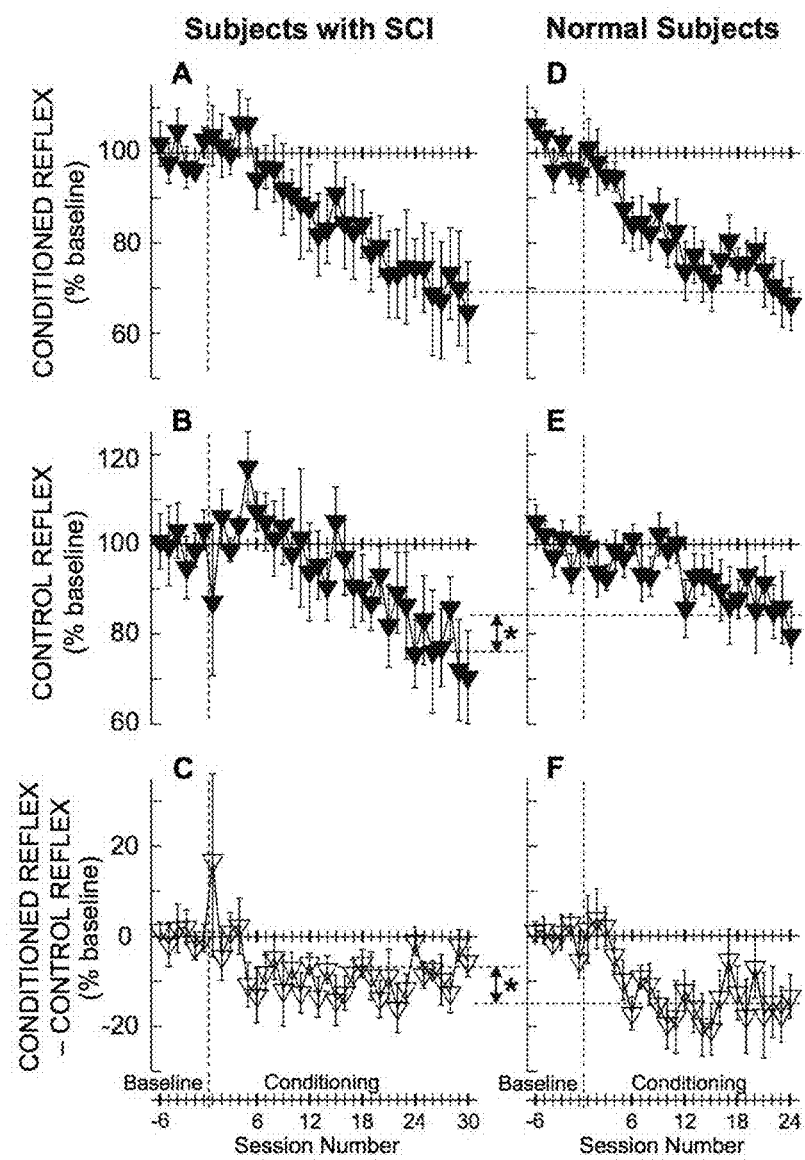
FIGS. 13A-13F: Average (±SE) H-reflex values for Baseline and Conditioning sessions for DC subjects with SCI (FIGS. 13A-13C, N=6, this study) and for normal subjects (FIGS. 13D-13F, N=8 (Thompson et al., 2009)) in whom the H-reflex decreased significantly.

FIGS. 13A-13F show the average courses of H-reflex changes for subjects with SCI (FIGS. 13A-13C; from this study) and for normal subjects (FIGS. 13D-13F; from Thompson et al. 2009) in whom down-conditioning was successful. FIGS. 13A and 13D show the Conditioned H-reflex change. FIGS. 13B and 13E show the Control H-reflex change. Finally, FIGS. 13C and 13F show the change in the within-session difference between the Conditioned and Control H-reflexes. This difference represents task-dependent adaptation; that is, the decrease that the subjects were able to produce immediately when they were asked to decrease the H-reflex.

These courses of change are noteworthy in several respects. First, the final average value of the Conditioned H-reflex (i.e., the average of the last 3 Conditioning sessions) in the subjects with SCI is identical to that in normal subjects (i.e., 69(±11SE)% and 69(±6)% of Baseline, respectively). Second, the final value of the Control H-reflex in the subjects with SCI is significantly smaller than in normal subjects (i.e., 76(±9)% of baseline vs. 84(±6)%, respectively (p=0.01, two-tailed t test)). Thus, the subjects with SCI decreased the Control H-reflex more than normal subjects. Third, like normal subjects, the subjects with SCI display an appropriate task-dependent adaptation (i.e., a session's average Conditioned H-reflex is smaller than its average Control H-reflex) that begins after four Conditioning sessions and remains about the same thenceforth. However, this task-dependent adaptation is significantly less in the subjects with SCI than in normal subjects (i.e., averages of −7(±3)% and −15(±6)%, respectively (p=0.01, two-tailed t test)). The greater decrease in the Control H-reflex in the subjects with SCI combines with their lesser task-dependent adaptation to yield a decrease in the Conditioned H-reflex that is identical to that found in normal subjects.

Four of the successful DC subjects completed Follow-up sessions one month and 3 months after the Conditioning sessions ended. At both one month and 3 months, the Conditioned H-reflex remained reduced in every subject, averaging 65(±10SE)% and 58(±10)% of baseline value, respectively. One DC subject also completed a 6-month Follow-up session. The Conditioned H-reflex was 26% of baseline, comparable to the value of 18% for the final three Conditioning sessions.

In the successful DC subjects, the $H_{max}$ measured at the beginning of each session also decreased with down-conditioning, paralleling the changes in the Control H-reflex (final value 84(±SSE)% of baseline, p<0.001, paired t test). In contrast, $H_{max}$ did not change significantly in the 7 subjects in whom the H-reflex did not decrease.

Locomotor Speed, Symmetry, EMG Activity, and H-Reflex Modulation Walking Speed Over the 30 Conditioning or Control sessions, the subjects' 10-m walking speeds increased by 0-123%. The increase was substantial and significant in the 6 DC subjects in whom the H-reflex decreased (+59(±19SE)%; p=0.03, paired t test). Furthermore, the two subjects who increased their walking speeds most also decreased their dependence on an assistive device in their daily lives: one switched from a walker to crutches and the other switched from a walker to a cane. In contrast, in the 7 subjects in whom the H-reflex did not decrease, walking speed increased less and not significantly (+25(±13)%; p=0.10). In none of these subjects did dependence on an assistive device change. FIG. 4A summarizes these results.

Locomotor Symmetry

Figures 14A, 14B, 14C:
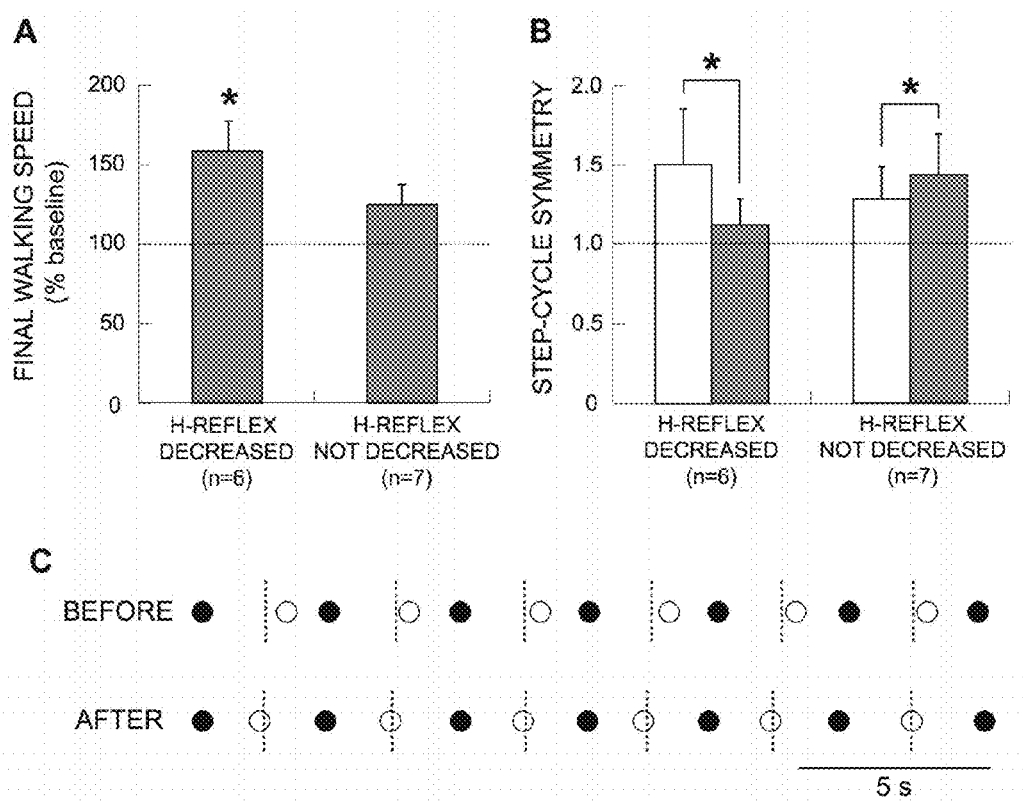
FIGS. 14A-14C.

To assess gait quality, we examined step-cycle symmetry (i.e., the ratio of the time between the nonconditioned leg's foot contact (nFC) and the conditioned leg's foot contact (cFC) to the time between cFC and nFC). A ratio of 1 indicates a symmetrical gait. During the Baseline period, the ratio was always >1 because foot drop and/or spasticity prolonged the swing phase of the conditioned leg (which was the more impaired leg) and/or because spasticity and the resulting instability in the conditioned leg shortened its stance (i.e., weight-bearing) phase. After the 30 Conditioning or Control sessions, this ratio decreased in every subject in whom the H-reflex decreased, becoming closer to 1 (p=0.05, paired t test). In contrast, the ratio increased in every subject in whom the H-reflex did not decrease (p=0.02). FIG. 14B summarizes these results. Thus, the successful DC subjects walked faster and more symmetrically; while the subjects in whom the H-reflex did not decrease walked slightly but not significantly faster and walked less symmetrically.

FIG. 14C shows the nFC-cFC and cFC-nFC time intervals in one DC subject before and after successful conditioning. Before conditioning, the nFC-cFC time interval was longer than the cFC-nFC interval. After conditioning, the two intervals were equal, indicating that locomotion had become more symmetrical.

Locomotor EMG Activity

To further assess changes in walking, locomotor EMG activity was recorded from the soleus, TA, vastus lateralis (VL), and biceps femoris (BF) muscles of both legs before and after the 30 Conditioning or Control sessions, and each muscle's Modulation Index (MI) was determined as described in the Methods.

MI values varied widely across subjects and across the 8 muscles of each subject, with many abnormally low values (i.e., >2 SD below the average for 12 normal subjects (Unpub. data)). In the DC subjects in whom the H-reflex decreased, the average MI rose significantly (from 74(±17SD)% to 80(±11)%) (p=0.005, paired t test). This improvement was bilateral; it was not limited to the muscles of the conditioned leg. Thus, successful H-reflex down-conditioning was associated with significant increase in the degree to which ankle and knee flexor and extensor muscles of both legs modulated their activity in synchrony with the step cycle. In the 7 subjects in whom the H-reflex did not decrease, the average MI did not change (84(±8)% before and 84(±10)% after) (p=0.25). (Although the average initial MI was higher in this group, it was still below normal (i.e., 89% (Unpub. data)). Thus, this lack of increase cannot be attributed simply to a ceiling effect.)

Figure 15:
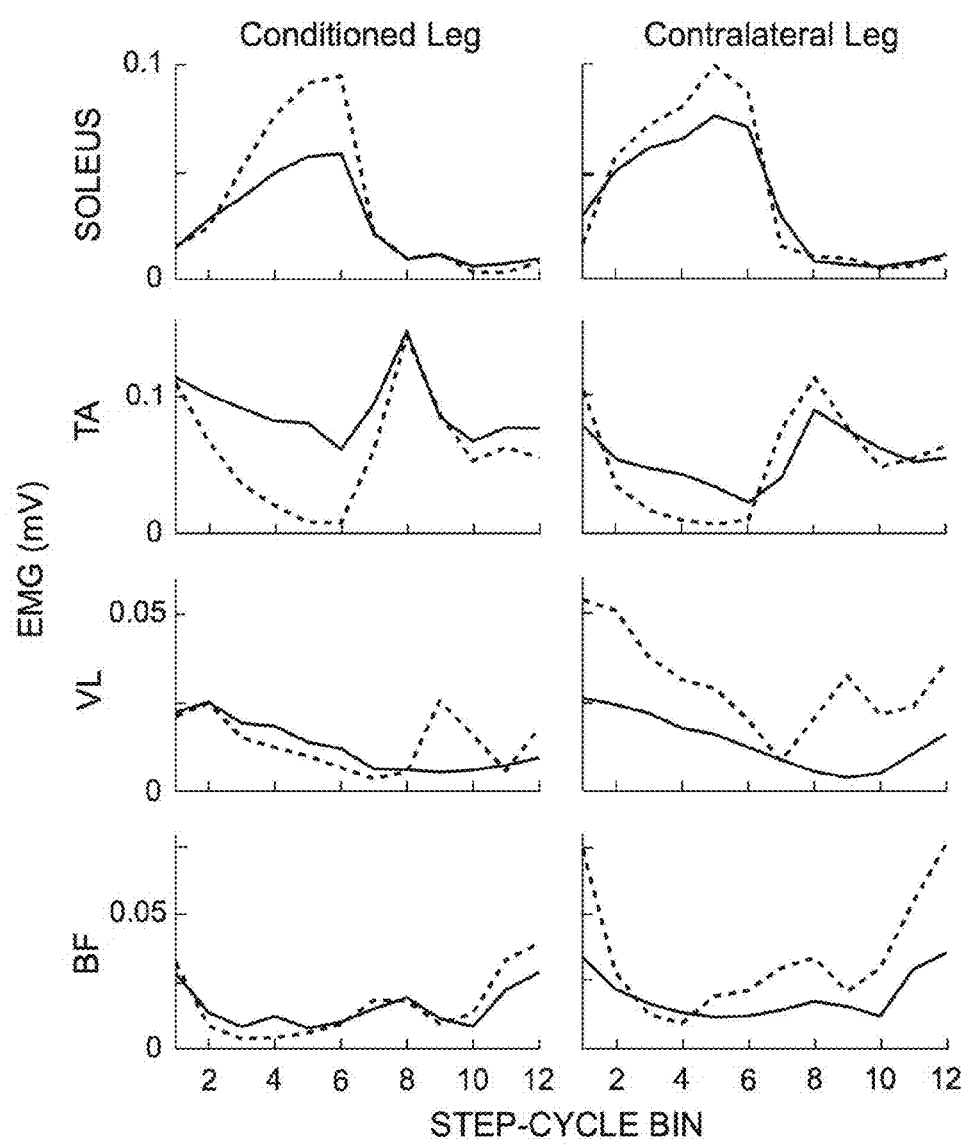
FIG. 15 are graphs showing locomotor EMG activity in soleus, tibialis anterior (TA), vastus lateralis (VL), and biceps femoris (BF) muscles of both legs before (solid) and after (dashed) conditioning in a DC subject with SCI in whom the soleus H-reflex decreased. The step cycle is divided into 12 equal bins, starting from foot contact. Thus, bins 1-7 are for the stance phase and bins 8-12 are for the swing phase. After successful down-conditioning, EMG modulation over the step cycle increases in both legs.

FIG. 15 shows modulation over the step cycle in the muscles of both legs for one DC subject before and after successful down-conditioning. After conditioning, soleus activity is increased and TA activity is decreased during mid-to-late stance in both legs. These bilateral improvements in the modulation of muscle activity controlling movement about the ankle joint probably resulted in more effective weight-bearing and push-off, and thereby contributed to this subject's increased walking speed (from 0.59 m/s to 0.80 m/s). Locomotor EMG modulation also increased in other muscles.

H-Reflex Modulation During Locomotion

In addition to recording EMG activity during undisturbed locomotion, we also elicited soleus H-reflexes during locomotion. As described above for locomotor EMG analysis, the step cycle was divided into 12 bins of equal duration and average H-reflex size for each bin was determined. The average of these 12 values defined the average locomotor H-reflex.

In the successful DC subjects, the average locomotor H-reflex also decreased (to 59(±17SE)% of baseline value; p=0.04 by paired t test). Thus, in humans as in rats (Chen et al., 2005; Chen et al., 2006b), an H-reflex decrease produced by the conditioning protocol was also evident during locomotion. The decreased average locomotor H-reflex reflected the combination of an overall decrease throughout the step cycle and a decrease concentrated in the swing phase, the period when the locomotor H-reflex is small in normal subjects. In contrast, in the subjects in whom the H-reflex did not decrease, the average locomotor H-reflex showed an insignificant increase (to 125(±17)% of baseline value, p=0.15).

Figure 16:
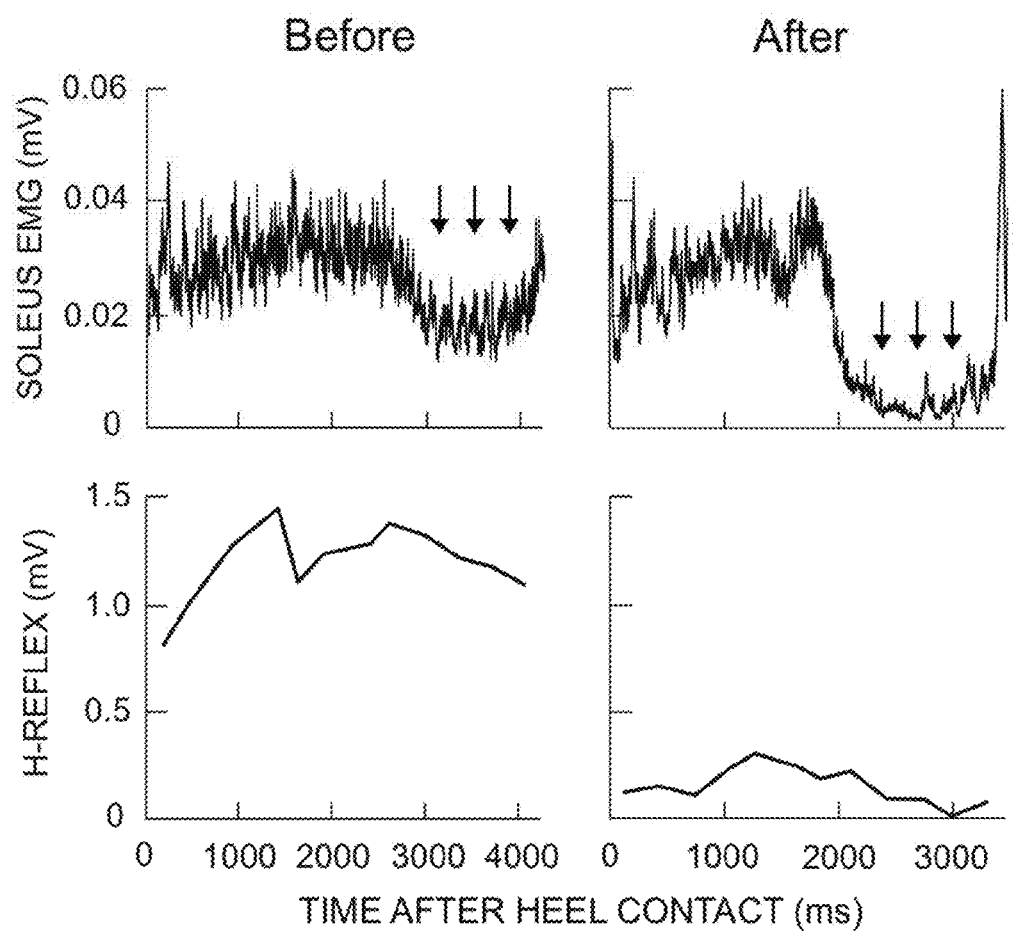
FIG. 16 are graphs showing rectified soleus EMG and locomotor H-reflex size over the step cycle before and after H-reflex down-conditioning in a DC subject with SCI in whom the H-reflex decreased. The reduced spasticity after conditioning produces better soleus EMG modulation: the abnormal activity during the swing phase (arrows) is no longer present. In addition, the locomotor H-reflex is greatly decreased and better modulated after conditioning (i.e., it is lowest during the swing phase).

FIG. 16 illustrates the decrease in the locomotor H-reflex of one successful DC subject. It is markedly reduced throughout the step cycle. In addition, its modulation across the step cycle has become more normal: the reflex is smallest during the swing phase. Locomotor soleus EMG has also become more normal, with much less inappropriate activity during the swing phase.

Spontaneous Subject Comments

Although subjects were not questioned about the current state of their disabilities during the study, many volunteered spontaneous comments. The 13 subjects made a total of 30 positive comments of 10 different kinds and no negative comments.

Figure 17:
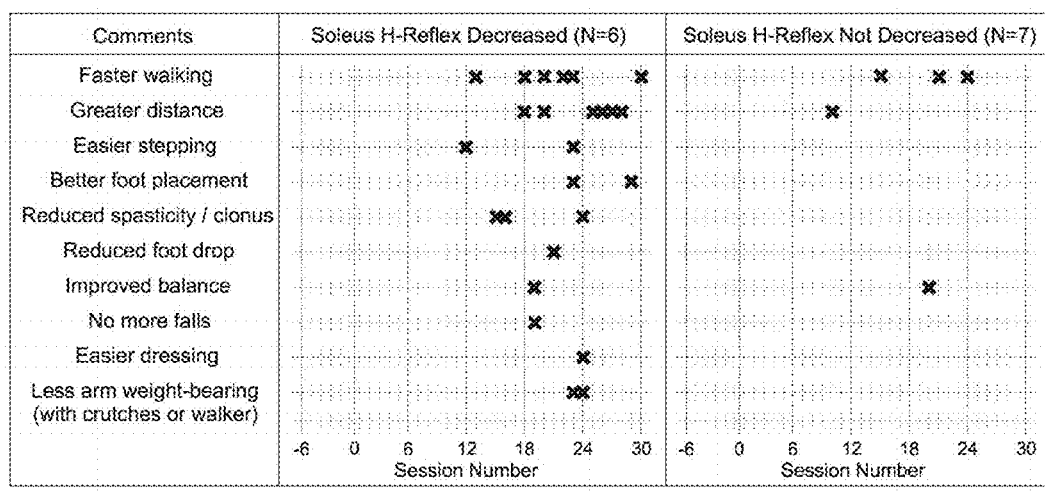
FIG. 17: Spontaneous comments made by subjects over the course of data collection. "x" indicates when a subject made the comment for the first time. Note that every subject in whom the H-reflex decreased reported walking faster and farther, and that these reports did not occur until substantial H-reflex decrease had occurred (i.e., FIGS. 13A-13F).

FIG. 17 lists these 10 different kinds of positive comments and indicates when during the study they were first made by the DC subjects in whom the H-reflex decreased significantly and by the subjects in whom the H-reflex did not decrease. The contrast is striking: 25 of the 30 positive comments were made by the 6 DC subjects in whom down-conditioning was successful and only 5 by the other 7 subjects (p=0.0027, Mann-Whitney U test). All 6 successful DC subjects reported walking faster and farther, and 1-3 of them made each of the other 8 positive comments. Furthermore, and most importantly, these comments did not occur until decrease in the Conditioned H-reflex was substantial and decrease in the Control reflex had begun (i.e., the 12th conditioning session and later; FIG. 13).

These spontaneous comments are consistent with the quantitative data showing that successful H-reflex down-conditioning was associated with faster walking, more symmetrical walking, better locomotor EMG modulation, and decreased locomotor H-reflexes. By showing that these objective effects were apparent to the subjects in their daily lives, the comments indicate that successful H-reflex conditioning had substantial practical impact.

Discussion

This study asked two questions. First, can people with chronic SCI and impaired locomotion decrease the soleus H-reflex in response to an operant conditioning protocol? Second, if so, is H-reflex decrease associated with improved locomotion? The results answer these questions clearly. First, people with incomplete SCI and impaired locomotion decreased the H-reflex in response to an operant down-conditioning protocol (DC subjects). Their success rate and magnitude of reflex change were comparable to those of people who were neurologically normal. H-reflex decrease was specific to the down-conditioning protocol; it did not occur in subjects in whom the H-reflex was simply elicited without feedback (UC subjects).

Second, H-reflex decrease was associated with faster and more symmetrical locomotion. The improvement was evident both in quantitative testing and, most important, to the subjects themselves in their daily lives. It did not occur in people in whom the H-reflex did not decrease, whether they were UC subjects or unsuccessful DC subjects. Indeed, locomotion became less symmetrical in every subject in whom the H-reflex did not decrease. (This greater asymmetry, combined with their slight increase in walking speed, suggests that these subjects expected to be walking faster after the 30 sessions, and thus walked slightly faster by taking more asymmetrical steps.)

These results indicate that reflex conditioning protocols might help to restore motor function after SCI or in other disorders. They also provide insight into the factors shaping the plasticity associated with H-reflex conditioning and into its potential therapeutic applications.

H-Reflex Conditioning in People with or without Spinal Cord Injury

The subjects with SCI were not significantly different from neurologically normal subjects (Thompson et al., 2009) in the probability of successful down-conditioning, and they were identical in the average magnitude of their H-reflex decrease (i.e., 31%). This finding is consistent with results for soleus H-reflex conditioning in spinal cord-injured rats (Chen et al., 2006b) and biceps spinal stretch reflex conditioning in people with SCI (Segal and Wolf, 1994).

The subjects with SCI did differ significantly from normal subjects in the composition of their final H-reflex change. Conditioned H-reflex change is composed of task-dependent adaptation (i.e., within-session difference between the Control H-reflex and the Conditioned H-reflex) plus long-term change (i.e., across-session change in the Control H-reflex) (Thompson et al., 2009). The former is thought to reflect immediate change in cortical influence (e.g., on presynaptic inhibition) while the latter reflects spinal cord plasticity. Task-dependent adaptation was significantly less in subjects with SCI than in neurologically normal subjects (−7% vs. −15%), while long-term change was significantly more (−24% vs. −16%). The lesser task-dependent adaptation in subjects with SCI may reflect damage to the corticospinal tract (CST), the spinal cord pathway principally responsible for H-reflex conditioning (Chen et al., 1996, 1999; Chen et al., 2002; Chen and Wolpaw, 2002), and may account for the slightly slower course of H-reflex decrease (i.e., over 30 sessions versus 24 in normal subjects (Thompson et al., 2009)).

The greater long-term change in subjects with SCI is more surprising. It may result from the fact that task-dependent adaptation affects the H-reflex pathway only during the conditioning protocol, while long-term change affects it continuously, and thus has much wider effects. Because the spinal cord serves many behaviors, spinal cord plasticity affects many behaviors. In neurologically normal subjects, the spinal cord plasticity responsible for the long-term change in the H-reflex is likely to disturb behaviors such as locomotion, which are already satisfactory; and it may thereby lead to additional plasticity that compensates for the change in the H-reflex pathway. Animal data support this inference. In normal rats, up- or down-conditioning of the soleus H-reflex increases or decreases, respectively, the soleus locomotor burst, but does not disturb the symmetry of the step cycle, suggesting that plasticity elsewhere preserves this symmetry (Chen et al., 2005). Indeed, in normal rats a conditioned change in the soleus H-reflex is usually accompanied by an opposite change in the quadriceps H-reflex, and also by changes in ankle and hip joint angles during locomotion (Chen et al., 2011). The angle changes are reciprocal, and help to ensure that hip height during stance does not change. It appears that in normal rats, and presumably in normal humans as well, compensatory plasticity prevents the plasticity responsible for the modified H-reflex from disrupting normal locomotion.

Furthermore, in normal subjects, the processes that preserve other behaviors may reduce the long-term plasticity that decreases the H-reflex. Wolpaw (2010) hypothesizes that spinal neurons and pathways are maintained in a state of "negotiated equilibrium," a balance that ensures the satisfactory performance of all the behaviors in the individual's current repertoire (Nielsen et al., 1993; Ozmerdivenli et al., 2002; Zehr, 2006). In normal subjects, the spinal cord plasticity underlying the new behavior (i.e., a smaller H-reflex) requires the creation of a new equilibrium that produces a smaller H-reflex and still continues to serve other behaviors satisfactorily. This new negotiation produces concurrent adaptive changes in the networks supporting the multiple behaviors that use the pathway. For behaviors such as locomotion, which are already satisfactory, these adaptations are likely to impede the long-term plasticity that decreases the H-reflex. The result is that, in normal subjects, much of the final change in the conditioned H-reflex is due to task-dependent adaptation, which does not disturb other behaviors.

In contrast, for subjects with SCI, the spinal cord plasticity responsible for the long-term H-reflex decrease improves locomotion, an important motor skill. Similarly, in rats in which a spinal cord injury has produced an asymmetrical step cycle, appropriate conditioning of the soleus H-reflex restores step-cycle symmetry (Chen et al., 2006b). In these SCI rats, as in the subjects of this study, the long-term change in the H-reflex is doubly adaptive: it increases reward probability in the conditioning protocol and it also improves locomotion. It creates a new spinal cord equilibrium superior to the one that prevailed before H-reflex conditioning. In sum, it is probable that long-term H-reflex change is greater in subjects with SCI than in normal subjects because it serves more than the new behavior, it also benefits locomotion.

Potential Therapeutic Applications of Reflex Conditioning Protocols

This study sought to down-condition the soleus H-reflex on the rationale that reducing the activity of this pathway would reduce the hyperreflexia that impaired locomotion in these subjects with incomplete SCI (Dietz and Sinkjaer, 2007; Nielsen et al., 2007). Successful down-conditioning did improve locomotion. Walking became faster and more symmetrical. Furthermore, the locomotor behaviors of knee and ankle extensor and flexor muscles in both legs became more strongly modulated in synchrony with the step cycle, which presumably contributed to the improvement in walking speed and symmetry.

These encouraging results are surprising in their breadth. It is unlikely that the plasticity underlying a smaller soleus H-reflex in one leg could itself have such broad beneficial effects on walking, including increasing the locomotor EMG modulation of contralateral muscles. This broad impact, combined with the animal data discussed above, implies that in these subjects with SCI, H-reflex conditioning triggered additional plasticity in other pathways important in locomotion, and thereby changed the entire behavior. These subjects had been injured 0.7-10 years earlier; and their locomotor deficits were stable. In this setting, the acquisition of a new behavior, a down-conditioned soleus H-reflex, disturbed the post-injury equilibrium that the injured spinal cord had reached. It apparently triggered widespread adaptive plasticity that produced a new equilibrium that both decreased the H-reflex and improved locomotion.

Because they can target particular spinal pathways and can either weaken or strengthen the activity of these pathways, reflex conditioning protocols can be designed to focus on each individual's particular deficits. The present study down-conditioned the soleus H-reflex because locomotion was impaired by hyperreflexia. In contrast, the Chen et al. (Chen et al., 2006b) study in spinal cord-injured rats up-conditioned the soleus H-reflex because locomotion was impaired by weak right stance. In both cases, the intervention was effective. This flexibility and specificity are distinctive and desirable features of this new therapeutic approach; and they distinguish it from less focused interventions such as botulinum toxin or baclofen, which simply weaken muscles or reflexes and may have undesirable side effects (Dario et al., 2004; Dario and Tomei, 2004; Sheean, 2006; Ward, 2008; Thomas and Simpson, 2012).

Reflex conditioning protocols might supplement therapies that involve repetition of complex behaviors (e.g., body-weight supported treadmill training (Edgerton et al., 2008), constraint-induced movement therapy (Taub and Uswatte, 2003; Wolf et al., 2006)). Indeed, H-reflex conditioning might be combined with treadmill locomotion so that subjects are rewarded for changing the reflex in a specific phase of locomotion. This combination might help restore normal reflex modulation across the step cycle (Stein and Capaday, 1988). The results of the present study also encourage therapeutic exploration of other reflex conditioning protocols. For example, in rats, reciprocal inhibition of soleus by common peroneal nerve stimulation can be increased or decreased by operant conditioning (Chen et al., 2006a).

Certainly, the dependence of reflex conditioning on the CST will affect its efficacy in people with SCI. On the American Spinal Injury Association Impairment Scale (AIS), the disabilities of the present subjects were rated C or D. Although their success rate was not significantly different from that of normal subjects (Thompson et al., 2009), it was lower; and the extent to which reflex conditioning is possible in people with more severe impairments is unclear. While future improvements in the conditioning protocol may increase success, the need for supraspinal input will remain. On the other hand, reflex conditioning may also prove useful for disorders in which the CST is not affected. For example, in rats in which peripheral nerve transection and reinnervation have produced disordered afferent connections, H-reflex up-conditioning can help to restore more normal reflex function (English et al., 2007).

Conclusions

In people with impaired locomotion due to chronic spinal cord injury, down-conditioning of the soleus H-reflex in the more impaired leg was associated with faster and more symmetrical locomotion. This improvement was apparent to the subjects in their daily lives. Similar improvement did not occur in subjects in whom the H-reflex did not decrease. Spinal reflex conditioning protocols that target each individual's specific deficits might supplement conventional rehabilitation methods and increase functional recovery.

Example 3

Preliminary Studies of the Effects of Soleus H-reflex Up-Conditioning on Locomotion in Rats after Sciatic Nerve Transection and Repair In rats in which the sciatic nerve has been transected and repaired, the nerve regenerates, however many peripheral sensory and motor axons do not reach their correct peripheral targets in muscles and sensory organs. As a result, locomotion is impaired: stance is weak on the impaired side and the rat limps. In preliminary studies, we have examined the locomotor impact of up-conditioning the soleus (SOL) H-reflex after sciatic transection and repair while regeneration was occurring. Rats were implanted with EMG electrodes in right SOL and tibialis anterior (TA) muscles and stimulating cuffs on the right posterior tibial nerve. After control data collection, the right sciatic nerve was transected and repaired. Beginning 2-10 days later, the rat was exposed for 120 days to either control-mode (i.e., transected and control-mode (TC rats)) H-reflex data collection, or to SOL H-reflex up-conditioning (i.e., transected and up-conditioning mode (TU rats)); and then treadmill locomotion was assessed. To date, the locomotor video data have been analyzed to determine average hindlimb joint angles and hindlimb length (i.e., distance from hip joint to base of toes) over the course of the step-cycle. Right hindlimb length was significantly greater in the TU rats than in the TN rats. In view of the abnormally flexed hindlimb position characteristic of sciatic transected/repaired rats, this finding implies that up-conditioning of the soleus H-reflex improved right leg extension during locomotion. We are now planning further studies aimed at further verifying this effect and examining the impact of up-conditioning on the entire behavior of locomotion. We anticipate that the results will provide new evidence in an another disorder (i.e., nerve injury) that an appropriate operant conditioning protocol that produces targeted neural plasticity can trigger general neural plasticity that improves all aspects of a complex CNS function such as locomotion.

Example 4

Preliminary Studies of the Effects of Sensorimotor Rhythm Conditioning on Hand/Arm Function Voluntary hand/arm movements are normally preceded by decreases in the amplitude of sensorimotor rhythms (i.e., 8-12 Hz mu rhythms and 18-30 Hz beta rhythms) in the EEG recorded from the scalp over the hand/arm region of contralateral sensorimotor cortex. These decreases are called "event-related desynchronization (ERD)." Sensorimotor rhythms are produced by thalamocortical/corticothalamic pathways. We are obtaining preliminary evidence that an operant conditioning protocol that increases the ERD prior to movement decreases reaction time and improves movement speed and accuracy. If these early results are confirmed, they will provide evidence that an operant conditioning protocol that produces appropriate targeted neural plasticity (TNP) in cortical/subcortical pathways can also trigger generalized neural plasticity (GNP) that improves a complex hand/arm behavior. Protocols of this kind could be used to enhance rehabilitation after strokes and other disorders that impair limb functions, and might also be used to improve limb functions beyond the normal range in people without disabilities.

REFERENCES

Citation of a reference herein shall not be construed as an admission that such reference is prior art to the present invention. All references cited herein are hereby incorporated by reference in their entirety. Certain references are cited by author and date. Below is a listing of various references cited herein, with the references being identified by author, date, publication, and page numbers:

C. Capaday et al., (1986) Journal of Neuroscience 6:1308-1313.
J. S. Carp et al., (1994) J Neurophysiol 72: 431-442.
J. S. Carp et al., (2006a) J Neurophysiol 96:1718-1727.
J. S. Carp et al., (2006b) Exp Brain Res 168:517-528.
X. Y. Chen et al., (1994) Brain Res 648:167-170.
X. Y. Chen et al., (1995) Journal of Neurophysiology 73:411-415.
X. Y. Chen et al., (1996) Journal of Neurotrauma 13:755-766.
X. Y. Chen et al., (1999) Journal of Neurotrauma 16:175-186.
X. Y. Chen et al., (2002) Experimental Brain Research 144:88-94.
X. Y. Chen et al., (2002) J Neurophysiol 87: 645-652.
X. Y. Chen et al (2006a) J Neurophysiol 96: 2144-2150.
Y. Chen et al., (2005) J Neurosci 25:6898-6906.
Y. Chen et al., (2006b) J Neurosci 26: 12537-12543.
Y. Chen et al., (2011) J Neurosci 31:11370-11375.
A. Dario et al., 2004) Drug safety: an international journal of medical toxicology and drug experience 27:799-818.
A. Dario et al., (2004) Journal of neurosurgical sciences 48:177-181.
V. Dietz et al., (2007) Lancet Neurol 6:725-733.
T. Drew et al., (2002) Brain Res Brain Res Rev 40:178-191.
V. R. Edgerton et al., (1997) Advances in Neurology 72:233-247.
V. R. Edgerton et al., (2001) J Physiol 533:15-22.
V. R. Edgerton et al., (2008) Brain Res Rev 57:241-254.
A. W. English et al., (2007) J Neurophysiol 97:1127-1134.
C. Ethier et al., (2003) Exp Brain Res 151:420-425.
S. J. Harkema et al., (1997) J Neurophysiol 77:797-811.
S. Harkema et al (2011) Principles and Practice. Oxford University Press.
H. Hultborn et al., (2007) Acta Physiol (Oxf) 189:111-121.
A. Kido et al., (2004a) J Appl Physiol 96:1969-1977.
A. Kido et al., (2004b) Can J Physiol Pharmacol 82:238-248.
L. Koski et al., (2004) Neurorehabil Neural Repair 18:230-249.
O. Lagerquist et al., (2006) Exp Brain Res 170:1-6.
R. L. Liu et al., (2010) Program No. 82.18. 2010 Abstract Viewer/Itinerary Planner. Washington, D.C.: Society for Neuroscience, Online.
M. Maegele et al., (2002) J Neurotrauma 19:1217-1229.
Y. Makihara et al., (2012) Muscle Nerve 45:116-125.
J. Nielsen et al., (1993) European Journal of Applied Physiology and Occupational Physiology 66:116-121.
J. B. Nielsen (2002) Brain Res Rev 40:192-201.
J. B. Nielsen et al., (2007) Acta Physiol (Oxf) 189:171-180.
T. Otis et al., (1996) J Neurosci 16: 7496-7504.
R. Ozmerdivenli et al., (2002) Physiol Res 51:395-400.
F. Pomerantz et al., (2010). Society for Neuroscience 40th Annual Meeting, Program No. 82.14.
S. Rossignol et al., (2011) Annu Rev Neurosci 34:413-440.
R. L. Segal et al., (1994) Exp Neurol 130:202-213.
G. Sheean (2006) Drug safety: an international journal of medical toxicology and drug experience 29:31-48.
R. B. Stein et al., (1988) Trends in Neurosciences 11:328-332.
E. Taub et al., (2003) J Rehabil Med: 34-40.
E. Taub et al., (1999) J Rehabil Res Dev 36:237-251.
G. W. Thickbroom et al., (2004) Clin Neurophysiol 115: 2144-2150.
A. M. Thomas et al., (2012) Muscle Nerve 46:443-448.

S. L. Thomas et al., (2005) J Neurophysiol 94:2844-2855.
A. K. Thompson et al., (2009a) Journal of Neuroscience, 29 5784-5792.
A. K. Thompson et al (2009b) Neurorehabilitation and Neural Repair, 23:133-142.
A. B. Ward (2008) J Neural Transm 115:607-616.
A. Wernig et al., (1992) Paraplegia 30:229-238.
A. Wernig et al., (2000) Prog Brain Res 128:89-97.
S. L. Wolf et al., (1996) J Neurophysiol 75:1637-1646.
S. L. Wolf et al., (2006) Jama 296:2095-2104.
J. R. Wolpaw (1987) J Neurophysiol 57:443-458.
J. R. Wolpaw (1997) Trends Neurosci 20: 588-594.
J. R. Wolpaw (2010) The Neuroscientist 16: 532-549.
J. R. Wolpaw et al., (1982) Brain Res 244:365-369.
J. R. Wolpaw et al., (1983) J Neurophysiol 50: 1296-1311.
J. R. Wolpaw et al., (1984) J Neurosci 4:2718-2724.
J. R. Wolpaw et al., (2009) Squire L R (ed.) Encyclopedia of Neuroscience, Oxford: Academic Press, volume 7, pp. 225-233.
J. R. Wolpaw et al (1989) J Neurophysiol 61: 563-572.
C. L. Yen et al., (2008) Neurorehabil Neural Repair 22:22-30.
E. P. Zehr (2006) J Appl Physiol 101:1783-1794.
E. P. Zehr et al., (2001) Journal of Physiology 537:1033-1045.
E. P. Zehr et al., (2012) Clin Neurophysiol 123:796-807.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A system for restoring or improving nervous system function of a subject, said system comprising a device comprising:
    (a) a nerve stimulation-electromyographic recording component comprising a nerve stimulator for stimulating a primary targeted central nervous system (CNS) pathway in a subject, at least one stimulating electrode array in functional communication with the nerve stimulator and adapted for topical contact with the subject, and at least one electromyographic (EMG) recording electrode array for recording EMG data of the subject produced in response to the stimulation of the primary targeted CNS pathway; and
    (b) a controller for operating the nerve stimulation-electromyographic recording component in accordance with an operant conditioning protocol, wherein said operant conditioning protocol is effective to produce targeted neural plasticity (TNP) in the primary targeted CNS pathway of the subject;
    wherein the subject is a human subject.

2. The system according to claim 1, wherein the nerve stimulator comprises an apparatus for providing a current or voltage pulse of selectable polarity, duration, and strength at externally triggered times through a pair of skin-mounted electrodes selected from a stimulating electrode array.

3. The system according to claim 1, wherein the at least one stimulating electrode array comprises one or more possible pairs of stimulating electrodes.

4. The system according to claim 1, wherein the at least one EMG recording electrode array comprises one or more possible pairs of EMG recording electrode arrays.

5. The system according to claim 1, wherein the operant conditioning protocol is effective to also elicit generalized neural plasticity (GNP) in one or more other CNS pathway, and wherein the elicitation of the GNP in the one or more other CNS pathway serves to restore or improve a nervous system function of the subject.

6. The system according to claim 1, wherein the controller comprises a computer processor and corresponding software effective to perform the operant conditioning protocol on the subject.

7. The system according to claim 6, wherein the software evaluates all possible pairs of stimulating electrodes to choose the most effective pair.

8. The system according to claim 6, wherein the software evaluates all possible pairs of soleus muscle recording electrodes to choose the most effective pair.

9. The system according to claim 6, wherein the software automatically adjusts stimulus strength as needed to maintain a target M wave or other target response.

10. The system according to claim 6, wherein the software automatically adjusts the amplitude criterion for reward as needed to maintain an appropriate reward frequency.

11. The system according to claim 6, wherein the software notifies the subject of any problem in EMG recording, in the responses obtained, or in other aspects of operation, and provides instructions and oversight for resolving the problem.

12. The system according to claim 6, wherein the software automatically adjusts stimulus strength as needed to maintain a target M wave.

13. The system according to claim 1, wherein the controller comprises a monitoring component effective to provide real-time feedback to the subject during performance of the operant conditioning protocol.

14. The system according to claim 13, wherein the monitoring component is effective to provide visual real-time feedback, audio real-time feedback, both visual and audio real-time feedback, and/or other sensory real-time feedback to the subject.

15. The system according to claim 1, wherein the controller is in communication with the nerve stimulation-electromyographic recording component.

16. The system according to claim 1, wherein the controller provides the subject with complete and appropriately illustrated instructions for donning and doffing the device, parameterizing the operant conditioning protocol, performing the operant conditioning protocol, and handling associated details selected from the group consisting of data storage and Internet-based interaction with a therapist.

17. The system according to claim 1, wherein the device further comprises:
    a wearable placement component for positioning the at least one stimulating electrode array at a stimulation target area of the subject and/or for positioning the at least one EMG recording electrode array at an EMG recording target area of the subject.

18. The system according to claim 17, wherein the stimulation target area of the subject is an area of the skin of the subject suitable for stimulating the primary targeted CNS pathway in the subject.

19. The system according to claim 17, wherein the EMG recording target area of the subject is an area of the skin of the subject suitable for facilitating the recording of the recording EMG data of the subject produced in response to the stimulation of the primary targeted CNS pathway.

20. The system according to claim 1, wherein the device further comprises:

a wireless communication device for receiving, displaying, storing, and/or analyzing data generated by the controller.

21. The system according to claim 20, wherein the wireless communication device is selected from the group consisting of a computer, a computer tablet, a personal digital assistant (PDA), a mobile phone, a portable digital media player, a personal eyewear apparatus for receiving and displaying data generated by the controller, and a dedicated digital device for receiving and displaying the data generated by the controller.

22. The system according to claim 1 further comprising:
a system component in functional communication or functional combination with said device, wherein said system component is effective to enable functioning of the device by the subject.

23. The system according to claim 22, wherein said system component comprises a portable device that communicates with the Internet via the cloud.

24. The system according to claim 22, wherein said system component comprises a programmable multichannel switch that connects a subset of stimulation electrodes to a positive and negative output of the nerve stimulator.

25. The system according to claim 23, wherein said nerve stimulator delivers single or trains of 1-50 mA current pulses that have a duration of about 0.1-1 ms and are triggered by said operant conditioning protocol.

26. A method for restoring or improving nervous system function of a subject, said method comprising:
(a) providing a system according to claim 1 for restoring or improving nervous system function of a subject; and
(b) using said system to administer the operant conditioning protocol to the subject under conditions effective to elicit TNP in the primary targeted CNS pathway and to elicit generalized neural plasticity (GNP) in one or more other CNS pathways,
wherein the elicitation of the GNP in the one or more other CNS pathway serves to restore or improve a nervous system function of the subject.

27. The method according to claim 26, wherein the operant conditioning protocol is self-administered by the subject.

28. The method according to claim 26, wherein the operant conditioning protocol is designed to down-condition hyperactive reflexes in the subject, up-condition hypoactive reflexes in the subject, and/or up-condition or down-condition other CNS pathways.

29. The method according to claim 26, wherein the primary targeted CNS pathway is selected from the group consisting of a monosynaptic pathway of a spinal stretch reflex, a monosynaptic pathway of a Hoffman reflex (H-reflex), a spinal pathway of cutaneous reflexes, a corticospinal tract, a reciprocal thalamocortical pathway that produces electroencephalographic (EEG) sensorimotor rhythms (SMRs), and other CNS pathways.

30. The method according to claim 26, wherein the one or more other CNS pathway is selected from the group consisting of other spinal reflex pathways, other corticospinal connections, intracerebral connections, cortical-subcortical pathways, and other CNS pathways.

31. The method according to claim 26, wherein the restored or improved nervous system function is selected from the group consisting of locomotion (walking), withdrawal responses, hand control, wrist control, arm control, ankle control, reach-and-grasp control, postural control, balance control, attention, perception, reaction time or accuracy, emotional control, reading, arithmetic, memory, other cognitive functions, and other sensorimotor functions.

* * * * *